US012672829B2

(12) United States Patent
Gill et al.

(10) Patent No.: US 12,672,829 B2
(45) Date of Patent: Jul. 7, 2026

(54) SYSTEM FOR DETERMINING CHANGE IN POSITION OF AN IMPLANTED MEDICAL DEVICE WITHIN AN IMPLANT POCKET

(71) Applicant: Pacesetter, Inc., Sylmar, CA (US)

(72) Inventors: Jong Gill, Valencia, CA (US); Fady Dawoud, Studio City, CA (US)

(73) Assignee: Pacesetter, Inc., Sylmar (CA)

( * ) Notice: Subject to any disclaimer, the term of this patent is extended or adjusted under 35 U.S.C. 154(b) by 550 days.

(21) Appl. No.: 18/192,987

(22) Filed: Mar. 30, 2023

(65) Prior Publication Data

US 2023/0346258 A1 Nov. 2, 2023

Related U.S. Application Data

(60) Provisional application No. 63/363,757, filed on Apr. 28, 2022.

(51) Int. Cl.
*A61B 5/00* (2006.01)
*A61B 5/103* (2006.01)

(52) U.S. Cl.
CPC ............ *A61B 5/686* (2013.01); *A61B 5/0031* (2013.01); *A61B 5/103* (2013.01)

(58) Field of Classification Search
CPC ....... A61B 5/686; A61B 5/0031; A61B 5/103; A61B 5/1116; A61B 5/1121
See application file for complete search history.

(56) References Cited

U.S. PATENT DOCUMENTS

| | | | |
|---|---|---|---|
| 6,044,297 | A | 3/2000 | Sheldon et al. |
| 8,818,748 | B2 | 8/2014 | Hatlestad et al. |
| 2020/0364327 | A1* | 11/2020 | Shute ...................... G06F 3/017 |
| 2020/0380840 | A1* | 12/2020 | Galarneau ............. A61B 5/1117 |
| 2021/0030295 | A1* | 2/2021 | Shute .................... A61B 5/1118 |
| 2021/0085202 | A1* | 3/2021 | Radtke ................ A61B 5/0031 |
| 2022/0266025 | A1* | 8/2022 | Hareland ............... A61B 5/686 |

OTHER PUBLICATIONS

Extended European Search Report for related EP App. No. 23166258 dated Aug. 7, 2023 (7 pages).

* cited by examiner

*Primary Examiner* — Catherine M Voorhees
(74) *Attorney, Agent, or Firm* — Dean D. Small; Carroll, Hoette & Butscher, LLC

(57) ABSTRACT
A system for determining a change in position of an implanted medical device (IMD) within an implant pocket is provided. The system includes an accelerometer configured to be implanted in a patient, the accelerometer configured to obtain accelerometer data along at least one axis. The system also includes one or more processors configured to determine the patient is engaging in a determined activity over an activity period, and obtain the accelerometer data during the activity period. The one or more processors are also configured to identify postures of the patient and corresponding posture periods during the activity period based on the accelerometer data, determine a duration related to a non-standing posture identified from the postures identified, and identify a migration of the IMD within the implant pocket based on the duration of the non-standing posture exceeding a duration threshold.

21 Claims, 12 Drawing Sheets

SYSTEM FOR DETERMINING CHANGE IN POSITION OF AN IMPLANTED MEDICAL DEVICE WITHIN AN IMPLANT POCKET

CROSS-REFERENCE TO RELATED APPLICATIONS

This application claims the benefit of U.S. Provisional Application No. 63/363,757 filed Apr. 28, 2022, which is hereby incorporated by reference in its entirety.

BACKGROUND

Embodiments herein generally relate to a method of detecting a pathologic episode by using an accelerometer implanted within a patient.

A three-dimensional (3-D) accelerometer that is implanted in a patient may detect movement of the patient during day to day activities. For example, an accelerometer may be part of an implantable cardiac monitor (ICM) or within another similar implantable medical device (IMD) to detect rotation based on the position and/or orientation of the IMD.

After an IMD is implanted into an implant pocket, movements of the patient can result in migration of the IMD within the implant pocket through movement, rotation, or otherwise. The IMD positioning in the pocket, and the pocket itself can change characteristics, effecting measurements. In particular, despite being tightly secured within the pocket, the IMD can still move and reposition within the pocket, effecting the IMD reading. Additionally, fluid levels and tissue variances within the pocket similarly can cause reading variation for the IMD. When these reading fluctuations occur, the IMD can obtain an incorrect reading and trigger an inappropriate arrhythmia or brady episode suggesting that a patient's heart has temporarily stopped when instead a change in positioning in the pocket has occurred. As such, the migration of the IMD within the implant pocket may have undesirable clinical effect such as changes in sensing and defib characteristics that can lead to altered device therapy.

BRIEF SUMMARY

In accordance with embodiments herein, a system for determining a change in position of an implanted medical device (IMD) within an implant pocket is provided. The system includes an accelerometer configured to be implanted in a patient, the accelerometer configured to obtain accelerometer data along at least one axis. The system also includes a memory configured to store program instructions, and one or more processors. When the one or more processors execute the program instructions, the one or more processors are configured to determine the patient is engaging in a determined activity over an activity period, and obtain the accelerometer data during the activity period. The one or more processors are also configured to identify postures of the patient and corresponding posture periods during the activity period based on the accelerometer data, determine a duration related to a non-standing posture identified from the postures identified, and identify a migration of the IMD within the implant pocket based on the duration of the non-standing posture exceeding a duration threshold.

In one example, the one or more processors are further configured to determine the migration of the IMD within the implant pocket based on the accelerometer data, and suspend obtaining the accelerometer data when the migration exceeds a migration threshold. In one aspect, the migration threshold is a fifteen degree (15°) rotation. In another aspect, the one or more processors are further configured to recalibrate a reference standing measurement related to a standing posture after suspending the obtaining of the accelerometer data, and resume obtaining the accelerometer data in response to recalibration of the reference standing measurement. In one example, to recalibrate the reference standing measurement the one or more processors are configured to obtain plural readings along an x-axis, y-axis, and z-axis with the accelerometer during the activity period, determine a standard deviation for each of the plural readings, and update the reference standing measurement based on the plural readings. In another example, the plural readings along the x-axis, y-axis, and z-axis is at least ten readings along the x-axis, at least ten readings along the y-axis, and at least ten readings along the z-axis.

Optionally, the one or more processors are further configured to communicate an alert in response to identifying the migration of the IMD within the implant pocket. In one aspect, the one or more processors are further configured to automatically recalibrate a reference standing measurement related to a standing posture in response to identifying the migration of the IMD within the implant pocket. In another aspect, to automatically recalibrate the reference standing measurement, the one or more processors are further configured to obtain a long term average of x-axis, y-axis, and z-axis vector data from one or more previous activity periods. In one example, to determine the patient is engaging in the determined activity, the one or more processors are further configured to determine whether the patient is moving above a speed threshold, or determine physiological characteristics of the patient.

In accordance with embodiments herein, a computer implemented method for determining a change in position of an implanted medical device (IMD) within a patient is provided. The method includes determining the patient is engaging in a determined activity over an activity period, obtaining accelerometer data during the activity period, and identifying postures of the patient and corresponding posture periods during the activity period based on the accelerometer data. The method also includes determining a duration related to a non-standing posture identified from the postures identified, and identifying a migration of the IMD within the implant pocket based on the duration of the non-standing posture exceeding a duration threshold.

Optionally, the method also includes determining the migration of the IMD within the implant pocket based on the accelerometer data, and suspending obtaining the accelerometer data when the migration exceeds a migration threshold. In one aspect, the method also includes recalibrating a reference standing measurement related to a standing posture after suspending the obtaining of the accelerometer data, and resuming obtaining the accelerometer data in response to recalibration of the reference standing measurement. In another aspect, recalibrating the reference standing measurement comprises obtaining plural readings along an x-axis, y-axis, and z-axis with an accelerometer during the activity period, determining a standard deviation for each of the plural readings, and updating the reference standing measurement based on the plural readings. In one example, the plural readings along the x-axis, y-axis, and z-axis is at least ten readings along the x-axis, at least ten readings along the y-axis, and at least ten readings along the z-axis. In another example, the method includes communicating an alert in response to identifying the migration of the IMD within the implant pocket.

Optionally, the method includes automatically recalibrating a reference standing measurement related to a standing posture in response to identifying the migration of the IMD within the implant pocket. In one embodiment, the method also includes automatically recalibrating the reference standing measurement includes obtaining a long term average of x-axis, y-axis, and z-axis vector data from one or more previous activity periods. In one aspect, the method also includes determining the patient is engaging in the determined activity comprises determining whether the patient is moving above a speed threshold. In another aspect, determining the patient is engaging in the determined activity includes determining physiological characteristics of the patient.

DETAILED DESCRIPTION

Figure 1:
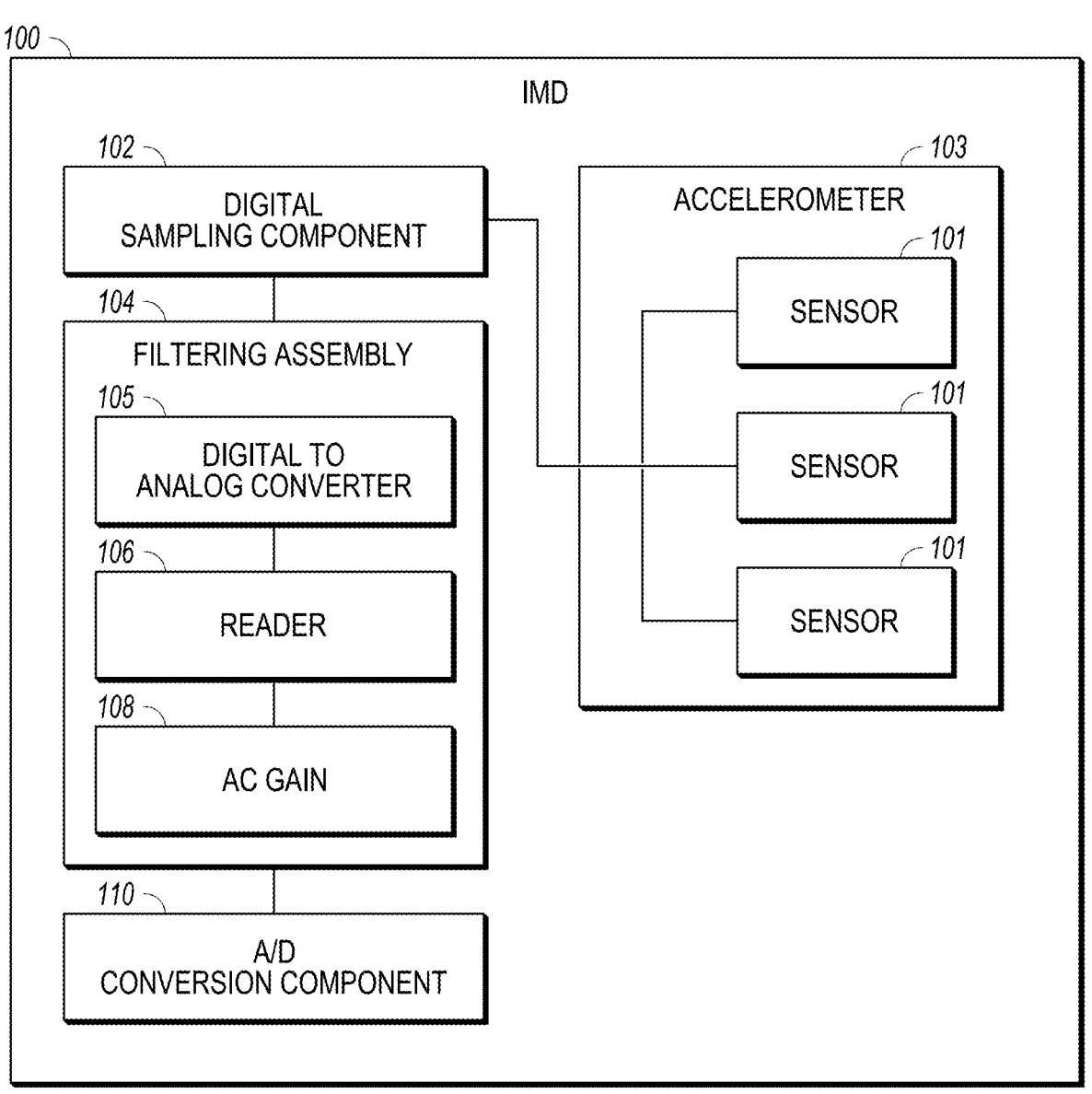
FIG. 1 illustrates a block diagram of an accelerometer formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "determined activity" shall mean any and all conditions, movements, exercises, or the like in which a patient is in a standing posture as would be detected by an accelerometer. Example activities include walking, jogging, running, playing sports such as tennis, racquetball, pickleball, basketball, soccer, golf, or the like. Such activities may include periods when a patient temporarily does not have a standing posture, such as tennis when a player must bend to hit a ball. Still when a patient is engaging in the determined activity, the patient has a standing posture for at least 80% of the duration of the activity period.

The term "activity period" shall mean any and all lengths of time in which a patient is engaging in a determined activity. Again, during the activity period there may be periods (e.g. posture periods) when a patient is not engaging in the determined activity, and as a result is not in a standing posture. Still, any length of time, or duration, when a standing posture of the patient is provided over 80% or more of the time is an activity period.

The term "standing posture" shall mean any and all postures of the patient when the patient is standing upright. The standing posture may be identified by an accelerometer reading when a patient is standing upright at an initial time.

The term "non-standing posture" shall mean any and all postures that are not a standing posture.

The term "migration" shall mean any and all movement, rotation, translation, etc. of an IMD from an initial position within an implant pocket. The initial position can be the position of the IMD when first placed in a patient within the implant pocket and an accelerometer reading is used to define the initial position, or the position of the IMD when an accelerometer is recalibrated, and the accelerometer is used to define an updated initial position.

The term "threshold migration" shall mean any all determined migrations that result in an alert, communication, recalibration, action, or the like. The threshold migration can be defined and/or provided as a movement, rotation, translation, etc. In one example, a fifteen degree (15°) rotation is a threshold migration. To this end, any determined rotation of 15° or more results in the alert, communication, recalibration, action, or the like to occur. Alternatively, the threshold migration could be 5°, 10°, 20°, or the like. Similarly, the threshold migration could be at least ten millimeters (10 mm), 20 mm, 30 mm, etc. in the implant pocket from an original position.

The term "reference standing measurement" shall mean a measurement provided by an accelerometer when an IMD is in an initial position and a patient is standing. The initial position can be the position of the IMD when first placed within the implant pocket of a patient and an accelerometer reading is used to define the initial position for a standing posture. Alternatively, the initial position can be the position of the IMD when an accelerometer is recalibrated, and the accelerometer is used to define an updated initial position for a standing posture. The reference standing measurement can include accelerometer data from one axis, two axes, or three axes. The reference standing measurement can be an average of accelerometer readings or data, a median of accelerometer readings or data, calculated, estimated, determined, or the like. The reference standing measurement can also be obtained from a combination of two or more axes measurements.

The term "alert" shall mean any communication that conveys information or data related to a migration of an IMD within an implant pocket. The communication can be an output on an output device, an electronic mail, a text message, an auditory message, etc. The communication does not have to contain information or data of a problem, danger, threat, or the like, and only conveys information and data related to a migration of an IMD within an implant pocket.

The term "long term average" shall mean data, information, measurement, calculation, determination, or the like utilized to update a reference standing measurement that is based on activity data stored in a memory of storage device of an IMD. To this end, the activity data is from more than determined activity that caused the migration of an IMD within an implant pocket to be determined, and instead at least in part of the activity data used to determine the long term average is activity data from a previous determined activity.

The term "IMD" shall mean an implantable medical device. Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973, 195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support, and/or merely monitor one or more physiologic characteristics of interest (e.g., PAP, CA signals, impedance, heart sounds).

Additionally or alternatively, embodiments herein may be implemented in connection with an integrated healthcare patient management system or network, such as described in "METHODS, DEVICE AND SYSTEMS FOR HOLISTIC INTEGRATED HEALTHCARE PATIENT MANAGE- MENT", provisional application 62/875,870, filed Jul. 18, 2019, which is incorporated by reference herein in its entirety.

Additionally or alternatively, embodiments herein may be implemented in connection with the methods and systems described in "METHOD AND SYSTEM FOR HEART CONDITION DETECTION USING AN ACCELEROM-ETER", Provisional Application No. 63/021,775, which is incorporated by reference herein in its entirety.

Additionally or alternatively, embodiments herein may be implemented in connection with the methods and systems described in "METHOD AND DEVICE FOR DETECTING RESPIRATION ANOMALY FROM LOW FREQUENCY COMPONENT OF ELECTRICAL CARDIAC ACTIVITY SIGNALS", U.S. application Ser. No. 16/869,733, filed on the same day as the present application, which is incorporated by reference herein in its entirety.

Additionally or alternatively, the IMD may represent or operate in conjunction with a body generated analyte test device or "BGA test device" which represents any and all equipment, devices, disposable products utilized to collect and analyze a BGA. The IMD may implement one or more of the methods, devices and systems described in the following publications, all of which are incorporated herein by reference in their entireties: U.S. Pat. No. 8,514,086, entitled "DISPLAYS FOR A MEDICAL DEVICE", issued Aug. 20, 2013; U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THERE-FORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", pub-lished Jun. 30, 2011; U.S. Pat. No. 5,294,404, entitled "REAGENT PACK FOR IMMUNOASSAYS" issued Mar. 15, 1994; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publi-cation Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMU-NOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169, which are hereby incorporated by reference in their entireties.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, infor-mation, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are communicated from an IMD and/or a remote server. The obtaining operation may be from the perspective of a remote server, such as when receiving the data, signals, information, etc. at a network interface from a local external device and/or directly from an IMD. The remote server may also obtain the data, signals, infor-mation, etc. from local memory and/or from other memory, such as within a cloud storage environment and/or from the memory of a workstation or clinician external programmer.

The terms "processor," "a processor", "one or more processors" and "the processor" shall mean one or more processors. The one or more processors may be imple-mented by one, or by a combination of more than one implantable medical device, a wearable device, a local device, a remote device, a server computing device, a network of server computing devices and the like. The one or more processors may be implemented at a common location or at distributed locations. The one or more pro-cessors may implement the various operations described herein in a serial or parallel manner, in a shared-resource configuration and the like.

Provided is the utilization of an accelerometer of an IMD that detects migration of the IMD within the implant pocket. In addition to having a posture detection algorithm devel-oped for patient heart failure status monitoring, an acceler-ometer also includes an algorithm for determining move-ments, including migration of the IMD within the implant pocket. In one example, the migration of interest is a rotatory (e.g. rotation-like) migration instead of straight slide migra-tion. The rotatory migration detection is especially impor-tant because the subsequent posture prediction algorithm that uses three dimensional (3D) accelerometer data can become invalid if the device rotation is too significant. As a result, the IMD is configured to determine when an IMD is in a known position, such as when a patient has a standing posture (e.g. known posture) while engaging in a determined activity such as walking, jogging, etc. Once the determined activity is identified, the accelerometer determines the pos-ture of the patient from a detected position of the acceler-ometer. The detected position or posture can then be com-pared to the known position or posture, to determine whether a migration of the IMD within the implant pocket has occurred. In particular, if the detected position presents a migration that is greater than a threshold migration, an alert is provided to make a clinician aware of the migration. The threshold migration is set based on migrations that can result in incorrect detected characteristics, incorrect determined diagnoses, incorrect therapies, incorrect postures, or the like as a result of the migration. In one example, the threshold migration is a fifteen (15) degree rotation.

FIG. 1 illustrates a schematic diagram of a IMD 100. In one example, the IMD is or includes an accelerometer 103. In one embodiment the IMD 100 is an ICM. In one example, the accelerometer 103 may be a chip for placement in the IMD 100. In another embodiment, the accelerometer 103 is formed and operates in the manner described in U.S. Pat. No. 6,937,900, titled "AC/DC Multi-Axis Accelerometer For Determining A Patient Activity And Body Position," the complete subject matter which is expressly incorporated herein by reference.

In one embodiment, the accelerometer 103 includes sen-sors 101 that generate first (X), second (Y) and third (Z) accelerometer signals along corresponding X, Y and Z axes (also referred to as first axis accelerometer signals, second axis accelerometer signals and third axis accelerometer signals). The X, Y and Z axes accelerometer signals collectively define a three-dimensional (3D), or multi-dimensional (MD) accelerometer data set. While examples herein are described in connection with an accelerometer 103 that generates accelerometer signals along three orthogonal axes, it is recognized that embodiments may be implemented wherein accelerometer signals are generated along two or more axes, including more than three axes.

The IMD 100 may include sensors 101 that monitor and receive signals from the X, Y and Z axes. In one embodiment, the individual X, Y and Z signals are received by a digital sampling component 102 that receives a digital input. Coupled to the digital sampling component 102 is a filtering assembly 104 that may include a digital to analog converter 105 to form an alternating current (AC) signal, a reader device 106, and an AC gain device 108. While in this embodiment, the filtering assembly includes the devices provided, in other examples, other devices may be utilized to filter the digital input signal for processing.

The IMD 100 may also include an analog to digital conversion component 110, along with a position, or direct current (DC) component. In one example, the analog to digital conversion component may be an 8-bit analog to digital converter (ADC). The evaluation version of the monitoring system 100 may provide 3-axis (X and Y along the chip, Z normal to the chip) DC-coupled posture signal corresponding to 3 orthogonal directions as well as 3-axis AC-coupled activity signal. In one embodiment, each of the 6 signal may be sampled at 100 Hz and accumulated over 1 sec for a total of 12 signals ([X/Y/Z], [posture/activity], [100/1 Hz]). This MD accelerometer data may be used to describe embodiments herein.

While described as a digital signal in relation to FIG. 1, in other embodiments the signal may be an analog signal, filtered, amplified, etc. The accelerometer data signals may be recorded in a data storage of the accelerometer 103, of the IMD 100, of a remote device etc. Alternatively, the accelerometer data set may be collected from a remote device, or received from a storage device coupled to the accelerometer. To this end, the accelerometer data set may be a multi-dimensional accelerometer data set.

The accelerometer sensors 101 may collect accelerometer signals from two or more axes. The accelerometer signals may come from at least two of the X-axis, Y-axis, or Z-axis. In one example, the accelerometer signals may be collected from all three axes.

The IMD 100 may also include one or more processors for implementing algorithms that use accelerometer data. In one example, a diagnosis algorithm can be provided for detecting arrythmias, syncope, fainting, falls, strokes, heart attacks, or the like. In one example, the diagnosis algorithm is the diagnosis algorithm described and disclosed in U.S. Ser. No. 17/192,961 filed Mar. 5, 2021, entitled System For Verifying A Pathologic Episode Using An Accelerometer that in incorporated in full by reference herein.

In one example, the IMD 100 includes a three-dimensional (3D) accelerometer based posture algorithm that calculates parameters including extent of right (ETR) and extent of supine (ETS). The final posture of the patient can then be predicted, or identified, based on the values of ETR and ETS. The ETR provides the degree of the device tilting or flipping either to the left or right across the long axis. The expected ETR value should be close to zero when subjects have a standing posture as a result of being active such as when walking or running. This is quite obvious given the subjects will be standing straight during walk or running like determined activities.

The IMD 100 can also include a migration detection algorithm that detects migrations of the IMD above a threshold migration. If the ETR is greater than a fixed value when a patient is engaging in a determined activity, it is likely that there occurred a threshold migration. Once the threshold migration is detected, the initial x/y/z posture data used for standing calibration, the reference standing measurement, is no longer valid and a new set of valid x/y/z standing baseline data is needed to provide an updated reference standing measurement. In one example, autocalibration of the accelerometer 103 can be provided.

The autocalibration step after the threshold migration detection uses the x/y/z data collected during the activity period of the determined activity, and once a condition is met, the baseline x/y/z data for the standing baseline is updated. In one example the condition can be related to the standard deviation of readings obtained during an activity period. In addition, the supine baseline data for x/y/z is relatively unaffected by the threshold migration such that the original supine baseline data is kept even after rotatory migration.

In one example the threshold migration may be a 15 degree rotation or more. Bench test and human data analysis have demonstrated that a current posture prediction algorithm is valid up to 15 degree rotation, thus the migration detection algorithm is targeted to detect 15 degree rotation or more. In another example, the migration detection algorithm detects migrations of the IMD up to at least one-hundred and eighty degrees (180°) flip. In particular, while 180° flip result in a position that still allows accurate characteristic measurements, therapies, etc., notification of the migration is still desired to be known for additional clinical analysis. Still, for the 180° flip, the clinical implication for the IMD is minimal because laying-down, recline, and upright postures are still valid. However, it is still important to know the occurrence of 180° flip, especially for the heart failure monitoring algorithm. In one example, ninety degree (90°) flip detection is not pursued as it is very unlikely for this migration to occur in real situations, especially after the formation of encapsulation. As a result, to save battery life, the threshold migration in one example remains 15°. Though in other examples the threshold migration may be less, such as 5° or 10°, or more such as 20° or 25°, depending on the diagnosis algorithms, posture algorithms, and other algorithms utilizing the accelerometer data.

The migration detection algorithm in one embodiment tracks extent of right (ETR) values calculated during a determined activity. As indicated above, the expected ETR value should be close to zero when a patient is active such as walking or running. If the ETR value is greater than the threshold migration value during a determined activity, remedial actions may be undertaken. These remedial actions can include suspending posture readings using the accelerometer, or functions that rely on accelerometer data. Another remedial action can include communicating an alert to the patient, a clinician, etc. Yet another remedial action can be automatically recalibrating the accelerometer for the standing posture using accelerometer data from the activity period, and/or previous activity periods.

In one example, the determined activity is any motion, movement, advancement, or the like that is achieved at a rate of at least two miles per hour (2 mi/hr). In other examples, this rate, or speed threshold, may be lower depending upon the patient. In one embodiment, a determined activity rate may be set by a clinician and input into the IMD. In this manner, if a patient is sick, moves slower for any reason, etc., the determined activity rate can be lowered. Similarly, for a relatively healthy patient, the determined activity rate could be increased to ensure the one or more processors accurately determine the patient is active and in an upright position. In examples, determined activities include walking, jogging, running, or the like where the known posture of the patient will be upright.

In other examples, the one or more processors of the IMD can determine when a patient is engaging in a determined activity as a result of monitoring patient physiological characteristics, including heart rate, respiration rate, blood pressure, increases in heart rate or respiration rate, or the like. In some examples, the IMD can access a calendar of the patient that indicates a determined activity will occur. Alternatively, the patient can provide an input to the IMD that a patient is engaging in a determined activity. Similarly, if a patient is undergoing therapy, a clinician may provide an input to the IMD to indicate the patient in engaging in the determined activity. In another example, a clinician has the patient stand for a determined period of time obtains the ETR values during the determined period of time. In each instance, the IMD makes determinations that a patient is engaging in the determined activity.

As indicated, the one or more processors track the ETR values during the determined activity to identify if there are any unplausible postures that are detected for a determined period. As an example, when a patient is on a treadmill walking, the patient is expected to be upright. While a patient may step off the treadmill and reach down to pick something up, this only occurs during a limited period. So, in one example, sensors detect for a large majority of the time (e.g. at least 80%) of an activity period that the patient is upright during the determined activity. Such sensors can obtain a continuous heightened heart rate, increased breathing, etc. during the activity period. The periods during an activity period, or potential activity period when non-standing postures are detected, are posture periods. If during the activity period the accelerometer data indicates that the patient is supine, sitting, angled, etc. (e.g. has a posture period) for more than a determined period, such as more than a minute during a determined activity, then an indication is provided that migration of the IMD within the implant pocket has occurred.

The accelerometer data should indicate that the patient is upright during the entire determined activity, with only a sudden change on occasion. If the acceleration data does not provide such an indication, migration of the IMD within the implant pocket has occurred. Basically, while subject is in motion, it is highly unlikely that the duration of posture periods of non-standing postures (prone, right lateral recumbent, left lateral recumbent and supine) add up to an amount of time greater than the determined period. So, the subset of total duration of these non-upright posture periods can be used to improve accuracy or simplify real-time operations.

In one example, daily ETR values can be captured and stored. When the daily ETR value exceeds the threshold migration, that in one example represents a 15° rotation, a posture algorithm can be suspended to prevent incorrect, or invalid accelerometer data from being utilized. As indicated above, when the IMD is deemed to exceed 15° rotation, the posture prediction is no longer valid. When that happens, the posture algorithm and additional posture dependent features such as sleep detection and nighttime heart rate variability (HRV) measurement is suspended.

Figure 2A:
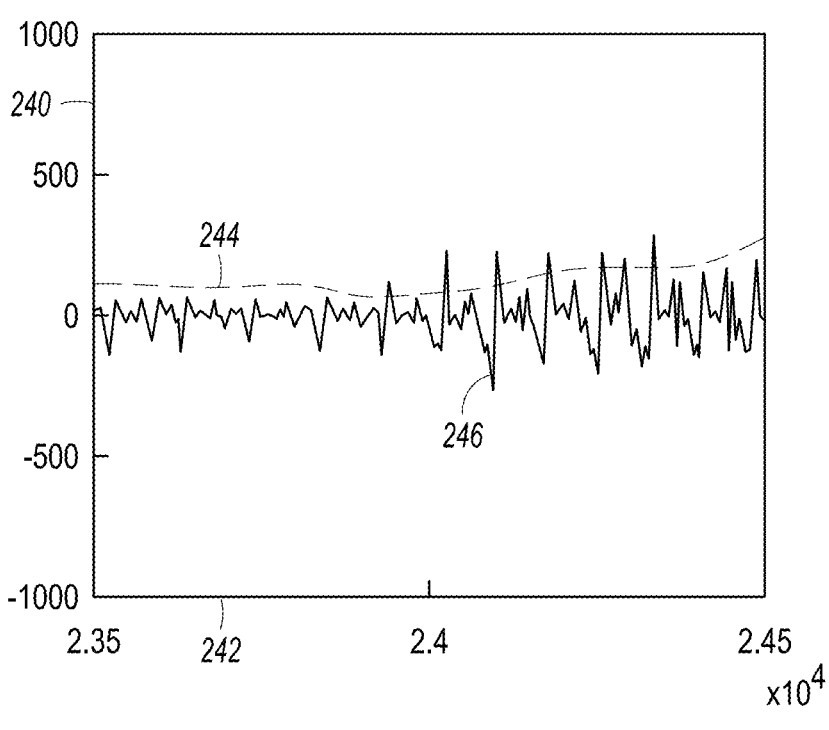
FIG. 2A illustrates a graph of activity over time in accordance with embodiments herein.
Figure 2B:
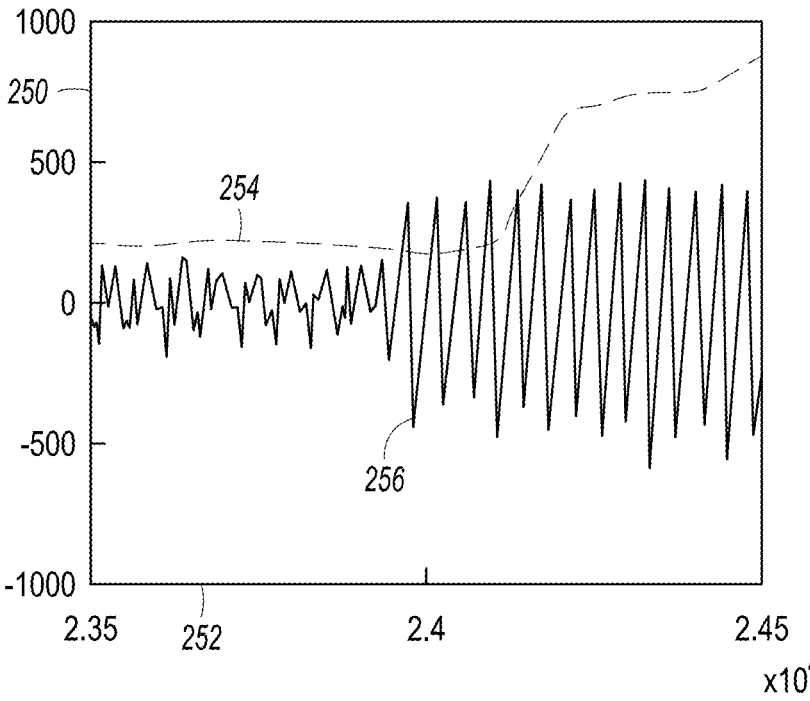
FIG. 2B illustrates a graph of activity over time in accordance with embodiments herein.
Figure 2C:
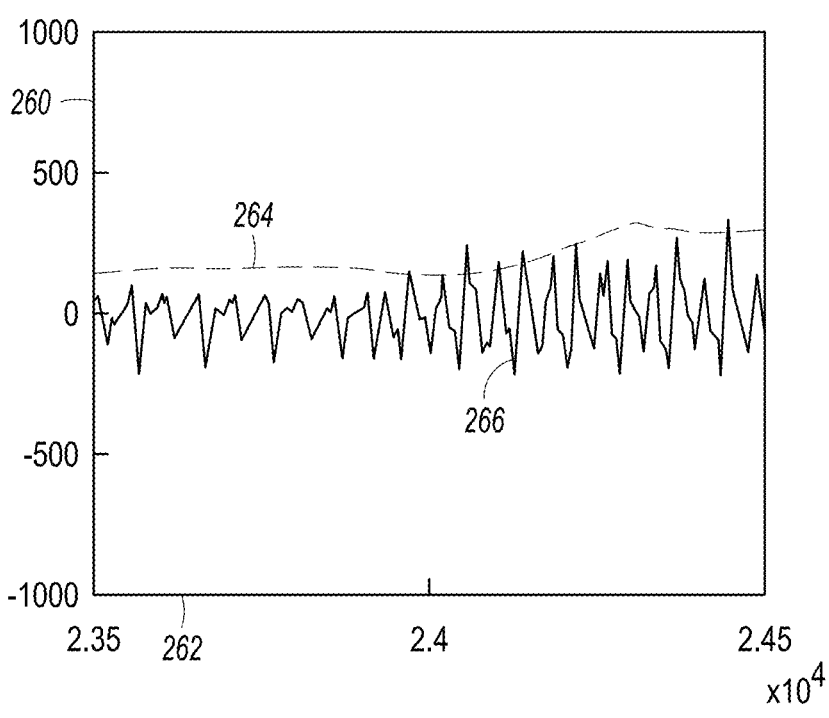
FIG. 2C illustrates a graph of activity over time in accordance with embodiments herein.

FIGS. 2A-2F illustrate example accelerometer signals that may be collected and recorded over 1 second intervals by the accelerometer 103 of the IMD 100 of FIG. 1. Specifically, IMD accelerometer signals may be collected and recorded, including both position related data sets and activity related data sets. Posture related data sets include the positions and changes in position of the patient along an X axis, Y axis, and/or Z axis. Activity related data sets include measurements related to the activity of the patient, including walking, running, jogging, or the like. FIG. 2A illustrates an activity level of the patient 240 over time 242 for the X axis, with activity of the patient over 1 second 244 monitored, along with 100 Hz activity of the patient over 1 second 246. Similarly, FIG. 2B illustrates activity level of the patient 250 over time 252 for the Y axis, with activity over 1 second 254 monitored, along with 100 Hz activity over 1 second 256. FIG. 2C meanwhile illustrates activity level of the patient 260 over time 262 for the Z axis, with activity level of the patient over 1 second 264 monitored, along with 100 Hz activity over 1 second 266.

Figure 2D:
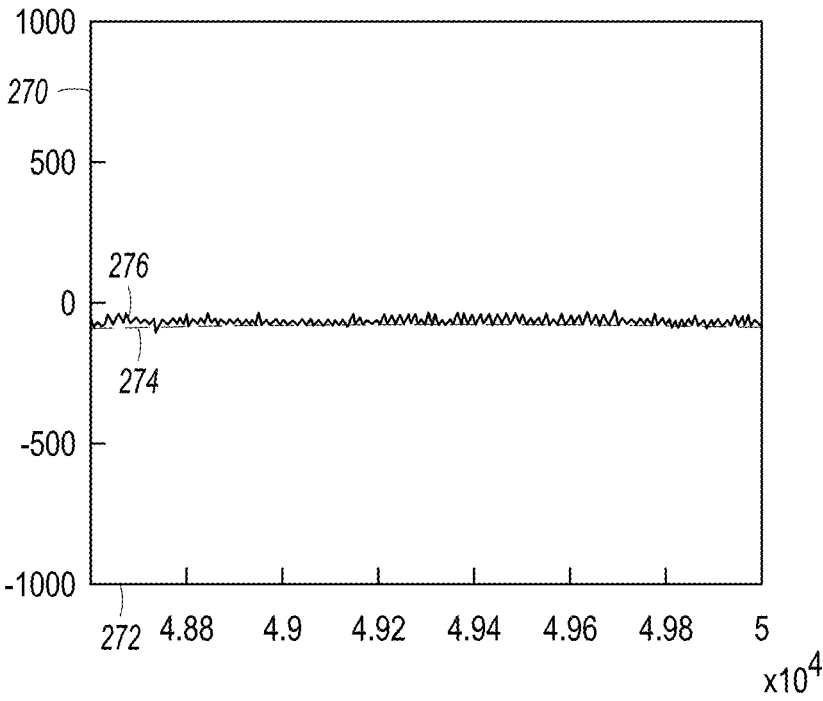
FIG. 2D illustrates a graph of position over time in accordance with embodiments herein.
Figure 2E:
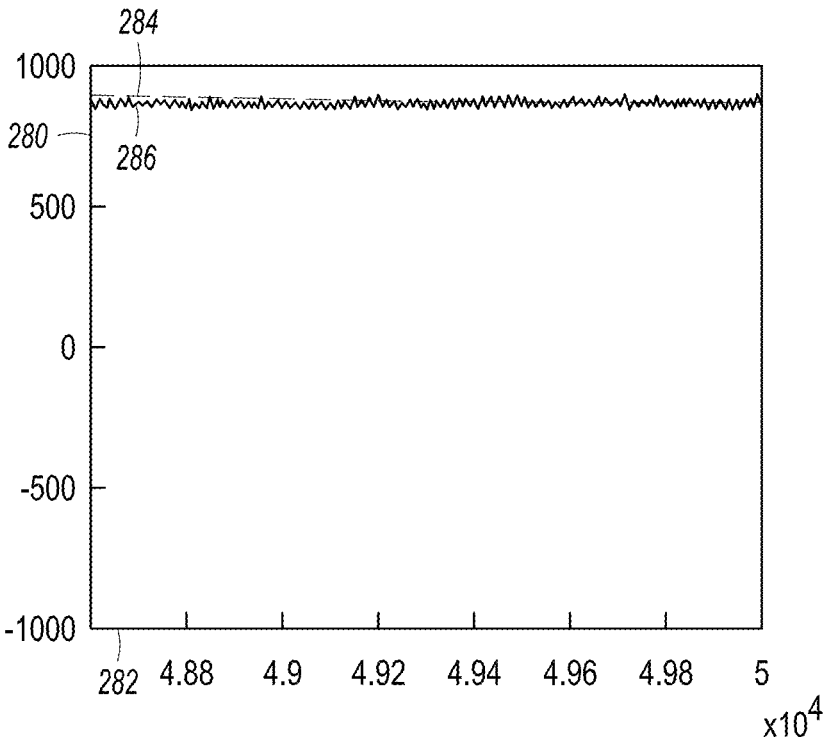
FIG. 2E illustrates a graph of position over time in accordance with embodiments herein.
Figure 2F:
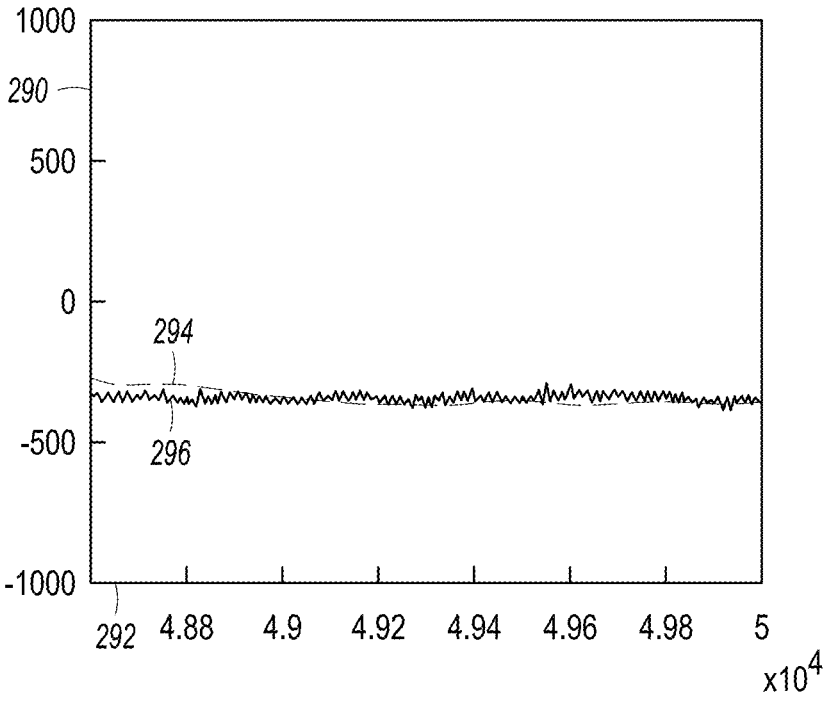
FIG. 2F illustrates a graph of position over time in accordance with embodiments herein.

In addition, or alternatively, as illustrated in FIGS. 2D-2F, posture may be monitored and recorded, including posture position 270 over time 272 for the X axis, wherein posture position over 1 second 274 along the X axis may be monitored along with posture position for 100 Hz over 1 second 276. Similarly, FIG. 2G shows posture position 280 over time 282 for the Y axis, including posture position over 1 second 284 along the Y axis along with posture position for 100 Hz over 1 second 286. Finally, for the Z axis, FIG. 2F illustrates posture position 290 over time 292, including posture position over 1 second 294 along with posture position for 100 Hz over 1 second 296.

Additionally or alternatively, in accordance with embodiments herein, the accelerometer signals and posture positions may be utilized to detect a change in position of the IMD.

Figure 3:
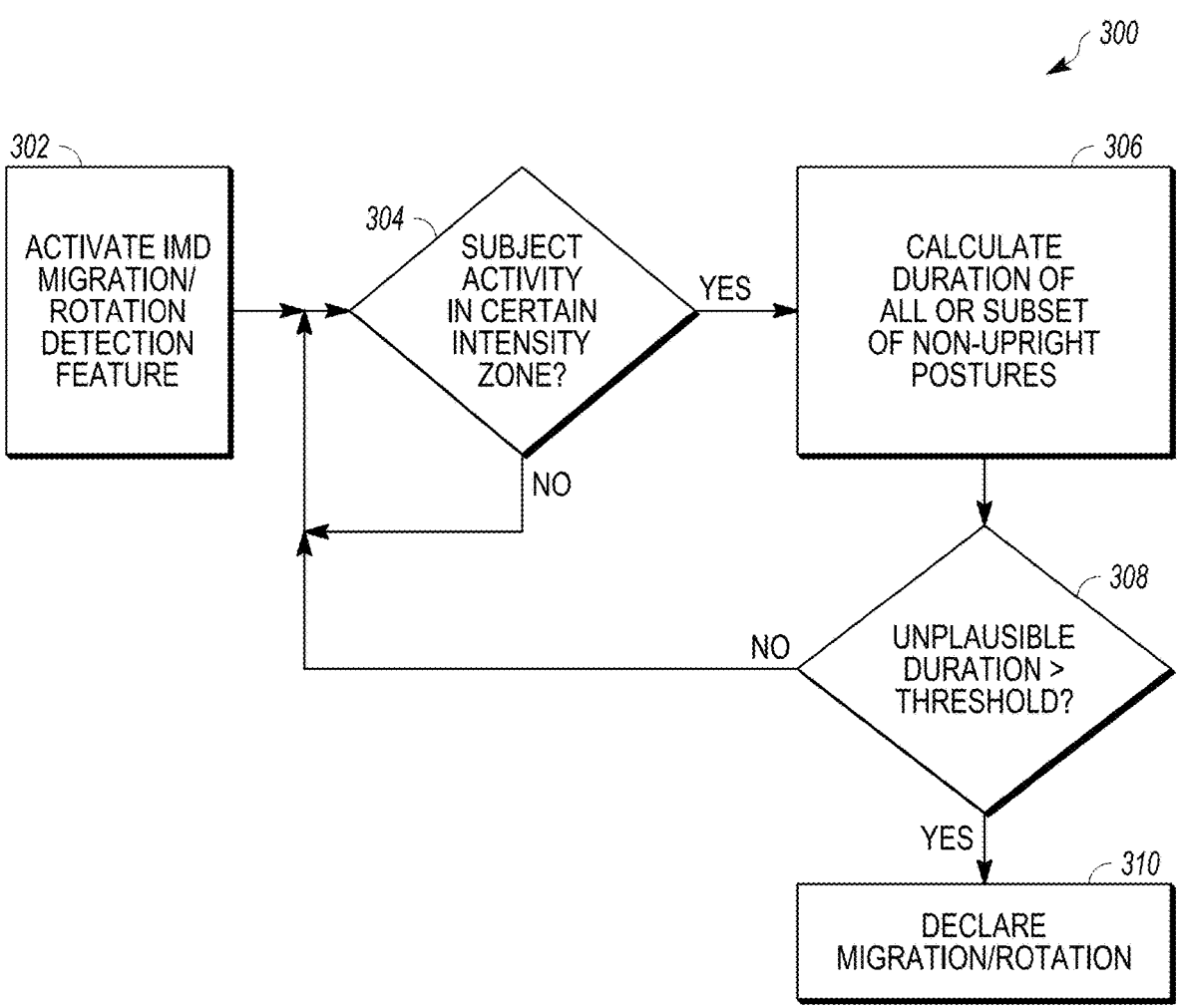
FIG. 3 illustrates a flow block diagram of a method of determining a migration of an IMD within an implant pocket in accordance with embodiments herein.

FIG. 3 illustrates a flow block diagram of a method 300 of determining a migration of an IMD within an implant pocket. In one example, the IMD 100 of FIG. 1 utilizing the accelerometer 103 is used to perform the method. In one example, the accelerometer can be a 3D accelerometer.

At 302, one or more processors activate an IMD migration or rotation detection feature to monitor the movements of the IMD within the implant pocket. In one example, instead of continuously collecting accelerometer data, the method includes only periodic checks to determine whether an IMD has migrated within the implant pocket beyond a migration threshold that would result in inaccurate diagnoses or treatments as a result of the migration. In one example, the IMD migration or rotation detection feature is only activated once a week, once every two weeks, once a month, or the like. Alternatively, instead of periodic activations that are automatically provided by the one or more processors, a clinician may select when to activate the IMD migration or rotation detection feature. In such an embodiment, the physician may utilize the IMD migration or rotation detection activation as part of a physical, checkup, etc., or in response to an event, including a cardiac event. Whether periodically activated, or activated a certain times, by not continuously obtaining and calculating acceleration data to check for migration within the implant pocket, battery life of the IMD is saved.

At 304, the one or more processors make a determination regarding whether a patient is engaging in a determined activity. In one example, patient data can be obtained from sensors, monitors, etc. such as the speed of the patient. If the speed of the patient is above a speed threshold, such as 2 mi/h, then a determination is made that during the time the speed of the patient remains above 2 mi/h, an activity period is provided. Sensors may also detect physiological characteristics of the patient such as heart rate, respiration rate, increased heart rate or respiration rate over a period. Again, such increased rates may result in a determination that a patient is engaging in a determined activity. In yet another example, the patient may provide an input into the IMD that a patient is engaging in a determined activity such as walking, jogging, running etc. Alternatively, a physician can input an activity is occurring at a visit. The physician may have the patient walk on a treadmill for a period such as ten minutes during a visit as part of a physical. The physician can then input the patient in undertaking the determined activity.

If at 304, a determination is made that a patient is engaging in a determined activity, then at 306, the one or more processors calculate the duration, or posture period, of all or all subsets of non-upright postures during the determined activity. During the determined activity, the patient is known to be in a standing position. Thus, if accelerometer data is obtained that indicates the patient is not in a standing position during an activity, an indication is provided that a migration of the IMD within the implant pocket has occurred. Still, during any determined activity, there may still be instances when a non-standing position will be detected. For example, if an individual is running during a workout and stops running, and continues walking, only with their hands on their knees for a short period before resuming walking. In this example, while bent over with hands on knees, the posture that is identified is not an upright posture, even though walking, a determined activity is occurring. In other examples, a patient may be playing a sport such as tennis where certain shots will result in a patient not being in a standing position. In other sports there may be period of time when an individual sits, bends over to get a drink from a water fountain, or the like that will result in a different posture being identified than an upright posture. Therefore, the posture periods of non-upright postures indicate such normal determined activity movements compared to when a migration of the IMD within the implant pocket has occurred. To this end, in one example, a migration is only determined when the posture obtained occurs during at least 80% of the activity period.

At 308, the one or more processors determine if the posture periods of the implausible (e.g. non-standing) postures are greater than a duration threshold. In particular, while on occasion during a determined activity a patient may bend over, sit, etc. for one reason or another, such non-standing postures should only temporarily occur during the determined activity. However, if a migration has occurred, then the non-standing posture will be identified as occurring throughout the activity. As a result, a threshold during may be provided that when exceeded indicates that a migration within the implant pocket has occurred. The duration threshold in one example is a percentage of the activity time. In one example, if over 50% of the determined activity time the patient is determined to be in a non-standing posture, a migration within the implant pocket is detected. In yet another example, the duration threshold is a set amount of time. So, in an example, if a non-standing posture is detected for longer than five straight minutes during a determined activity, the duration threshold is exceeded. In another example, the duration threshold may vary based on physiological characteristics determined during the determined activity. For example, a respiration and heart rate may be monitored, such that if patient is playing a sport where they sit to take a rest, a heart rate and respiration rate will decline during such activity. Consequently, the duration threshold may increase from five minutes to ten minutes to account of the reduce heart and respiration rates.

If at 308, the duration threshold is exceeded, then at 310, the one or more processors determine that an IMD migration within the implant pocket has occurred. Once a migration is determined to be presented, then additional processes may be undertaken, to address the migration. In some instances, the migration will not be enough to effect algorithms utilized to diagnosis physical conditions, postures, treatments or the like. Still, the detection of the migration within the pocket can result in more frequent checks to ensure the IMD does not migrate in the implant pocket to a migration threshold where the migration effects such algorithm accuracy. Alternatively, such a migration threshold may be reached resulting in suspension of the accelerometer data based diagnosis algorithms, treatment algorithms, posture algorithms, etc. until recalibration can occur.

Figure 4:
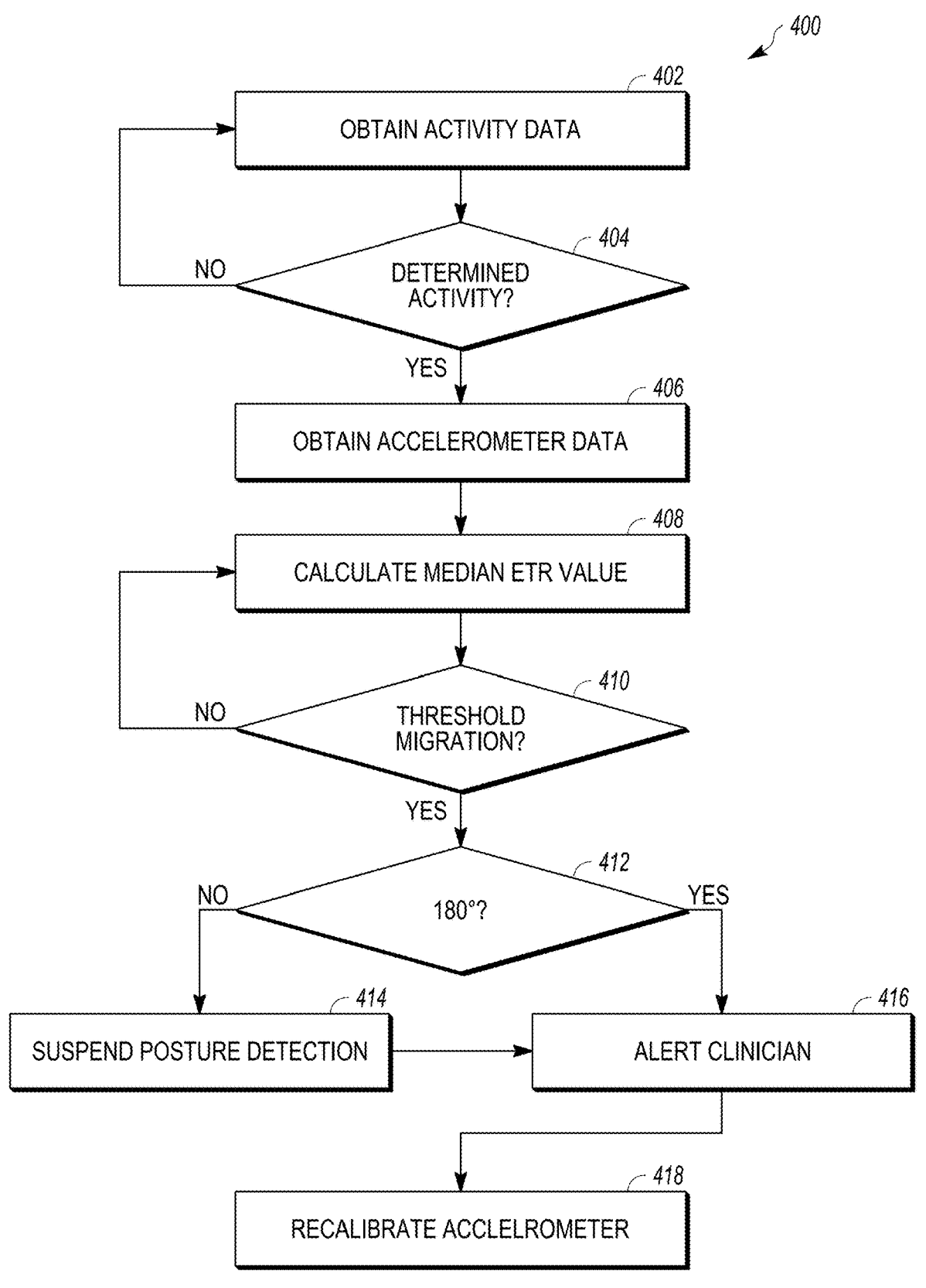
FIG. 4 illustrates a flow block diagram of a method of determining an extent of a migration of an IMD within an implant pocket in accordance with embodiments herein.

FIG. 4 illustrates a flow block diagram of an alternative method 400 of determining an extent of a migration of an IMD within an implant pocket that includes detection for a 180° migration. The IMD can include any IMD described herein, including the IMD of FIG. 1. The IMD can include an accelerometer, including a 3D accelerometer that is configured to obtain accelerometer data along an X-axis, Y-axis, and a Z-axis.

At 402, one or more processors on an IMD obtain activity data related to a patient. The activity data can include any signals, information, inputs, outputs, etc. that can be utilized to determine a patient is engaging in a determined activity, and in particular a determined activity that indicates the patient is in an upright position. The determined activity can include walking, jogging, skiing, skating, running, or the like. In one example, accelerometer data can be utilized to obtain the activity data. In another example, the IMD can obtain the activity data. For example, an IMD can monitor a heart rate, respiration rate, patient location, patient movement (including with a satellite navigation system), or the like. In another example, an electronic device in communication with the IMD can collect or obtain the activity data. For example, a smart watch, smart phone, IMD, FitBit®, or the like can detect activity data such as heart rate, blood pressure, respiration, patient speed, patient location, etc.

At 404, one or more processors make a determination whether a patient is participating in a determined activity based on the activity data. In one example, the speed of the patient is determined based on the activity data, and if the speed of the patient is above a speed threshold, such as 2 mi/h. In another example, an increased heart rate and respiration rate over a period may result in a determination that a patient is engaging in a determined activity. In yet another example, the patient may enter that a determined activity, such as a determined exercise is to begin. In each instance, a determination is made whether a determined activity is occurring. If a determination is made that a determined activity is not occurring, the one or more processors continue to monitor the activity data until a determination can be made that a determined activity is occurring.

If at 404 a determination is made that a patient is engaging in a determined activity, then at 406, the one or more processors obtain accelerometer data along at least one axis during the period of the determined activity, in addition to ETR values. The accelerometer data may include IMD accelerometer data, activity related data, posture related data, or the like. The accelerometer data may be obtained from any of the three axes in any manner described herein.

The posture related data of the accelerometer may similarly be obtained from any axis or may be a composite of the axes. The accelerometer may be programed to obtain the accelerometer data continuously during the activity period.

At 408, the one or more processors calculate a median ETR value for a determined period. In one example, the determined period is one day. In another example, the determined period may be twelve hours, forty-eight hours, seventy-two hours, or the like. By determining the ETR value, a determination is made regarding the migration of the IMD within the implant pocket. In particular, because during the activity period the patient is known to be upright, the ETR value provides the amount of rotation of the IMD from the initial position of the IMD. Once determined, the median ETR is stored in a storage device or memory.

At 410, the one or more processors determine if the median ETR value exceeds a threshold migration. In one example, the threshold migration is 15°. Alternatively, the threshold migration may be 12°, 18°, etc. The threshold migration is representative of the amount of migration of the IMD within the implant pocket before determinations, including diagnosis determinations, made based on accelerometer data is no longer valid. Once the IMD has rotated to the migration threshold, the accelerometer needs to be calibrated to ensure that any diagnosis, treatment, or the like remain accurate. In one example, if the median ETR is greater than 0.27, the threshold migration is provided. If the median ETR is within the threshold migration, then the one or more processors take no further action, other than continuing to continuously calculate the median ETR for a next determined period.

If at 410 the one or more processors determine the migration threshold is exceeded, then at 412, the one or more processors determine if a one-hundred and eighty degree (180°) rotation has occurred. While the migration of the IMD within the implant pocket over the threshold migration can result in incorrect diagnoses, treatments, etc., if the migration is a full 180°, the diagnoses, treatments, and other determinations utilizing the accelerometer data will still be accurate. Consequently, there is no need to suspend posture detection based on a 180° migration. Therefore, the one or more processors verify that the migration is not a 180° migration.

If at 412, a 180° migration within the implant pocket has not occurred, then at 414 the one or more processors suspend posture detection by the accelerometer, and all features of the IMD that rely on the posture measurements. Because of the migration in the implant pocket, until the accelerometer is recalibrated to base measurements on the new location, and/or position of the IMD, the accelerometer is shut down to ensure incorrect diagnosis, treatment, or the like do not occur.

At 416, the one or more processors communicates an alert to a clinician that a migration threshold has been exceeded. When the migration threshold has been exceeded and is at 180°, the alert informs the clinician of the 180° migration, and that accelerometer measurement have not been suspended. While the determinations made using the accelerometer data may not be affected by that 180° migration, other determinations, treatments, etc. may be affected. As a result, the clinician is alerted to the 180° migration. In examples of when an 180° migration in the implant pocket is not presented, the alert can also inform the clinician that the IMD is no longer collecting accelerometer data or making diagnoses, providing treatments, or the like based on accelerometer data. In one example, the alert may be an electronic mail message, text message, signal, or the like to make the clinician aware of the migration within the implant pocket. The alert may be provided through an application, a cloud, a clinician portal, etc. To this end, in addition to alerting the clinician, a message may also be communicated to the patient to set an appointment regarding the migration. To this end, in an example, the IMD may set the appointment and place the appointment on the calendar of the patient.

Optionally, at 418, the one or more processors recalibrate the accelerometer of the IMD. By automatically recalibrating the accelerometer, the IMD may automatically begin using the accelerometer again for making diagnoses, treatments, etc. A follow up appointment may still be scheduled and attended by the patient to verify the calibration. In particular, after the migration detection and auto recalibration, and alert, message, or the like is provided to either the patient or clinician to have an appointment so that the clinician and perform a real standing and supine reference vector capture, or other similar reference vector capture. Alternatively, new vectors can be captured at such an appointment. In this manner the method provides a manner to alert of the migration and recalibration occurrence and recommend a refresh of reference vectors at as soon as possible and an appointment.

Figure 5:
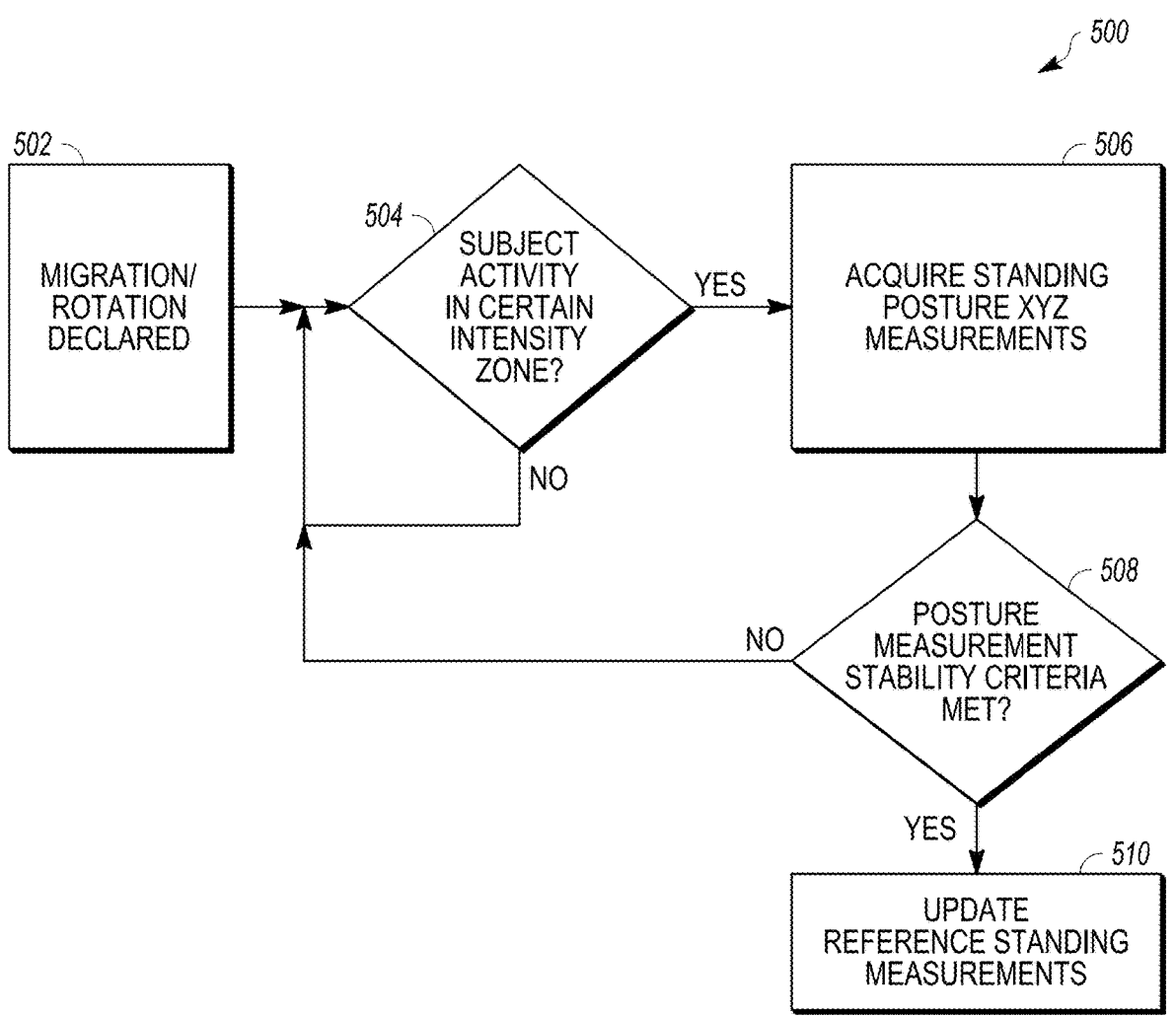
FIG. 5 illustrates a flow block diagram of recalibrating an accelerometer of an IMD in accordance with embodiments herein.

FIG. 5 illustrates a method 500 of recalibrating an accelerometer of an IMD after a threshold migration has been determined. In example embodiments the IMD of FIG. 1 is the IMD with the accelerometer that performs the method. In another example embodiment, this method is utilized at step 418 of the method of FIG. 4.

At 502, the one or more processors determine that the migration threshold has been exceeded and an undesired migration within the implant pocket has occurred. In one example, the method of FIG. 3 or FIG. 4 are utilized to determine that the migration threshold has been exceeded and an undesired migration has occurred.

At 504, the one or more processors determine if a patient is engaging in a determined activity. In one example the one or more processors may make the determination in any manner previously discussed, including the patient exceeding a determined speed threshold, utilizing physiological data such as heart rate, input from the patient, or the like.

At 506, if the one or more processors determine a patient is engaging in a determined activity, then at 508 accelerometer data is obtained for the activity period of the determined activity. In one example, accelerometer data is obtained for each of the x-axis, y-axis, and z-axis. The accelerometer data includes at least ten (10) readings from each axis. In other examples at least thirty-five (35) readings, fifty (50) readings, etc. from each axis are obtained. By obtaining and making calculations on multiple readings, including at least ten readings (or more) of each axis, a buffer is provided allowing the elimination of inaccurate data points. For example, an individual may be walking on a treadmill while watching television and have a remote to change the channels. While changing the channels the individual could drop the remote, resulting in them getting off the treadmill and bending over to pick up the remote. So, a reading could be taken while the patient is bending over to pick up the remote that is not consistent with the other readings. Similarly, while running or jogging an item can fall out of a pocket of a patient causing them to bend over to pick the item up. Alternatively, if a sport is being played, there may be periods of time during the sport where an individual sits to rest, changes positions, etc. that can provide inconsistent x/y/z accelerometer data compared to the rest of the activity. Therefore, by having numerous readings, the effect of such outlier readings is reduced and minimized.

At 510, the one or more processors determine if a posture measurement stability criteria is met. In particular, each set of ten or more readings are analyzed by averaging each set of data for each axes, and then determining the standard deviation for each reading of each axis. In one example, the highest and lowest readings of each set are automatically eliminated before averaging and standard deviations are determined. The purpose is to attempt to eliminate the outlier posture readings that result from picking up a remote, or something dropped out of a pocket, random non-upright movements during exercise, periods of sitting or laying down during an activity, or the like that results in the patient not being in a standing upright position during the period of time of the activity. Once the standard deviation for each axis is determined, each axis standard deviation can be added to provide a standard deviation for the three axes ($STD_{3axis}$). In this manner, the $STD_{3axis}$ is the posture measurement stability criteria such that if the $STD_{3axis}$ is above a deviation threshold, additional measurements are obtained. In one example, the additional measurements (e.g. acceleration data) are obtained from the period of time of the determined activity. In another example, a new determined activity must be determined, and the additional measurements (e.g. acceleration data) are obtained based on the new determined activity.

If at 510 the posture measurement stability criteria are met, then at 512, the one or more processors update reference standing measurements. In one example, the posture measurement stability criteria is the $STD_{3axis}$ calculation. In another example, the three axes are not added, and instead each axis has its own individual standard deviation threshold where each axis must meet this standard deviation threshold. So, if the x-axis standard deviation threshold is met, and the y-axis standard deviation threshold is met, but the z-axis standard deviation threshold is not met, the measurement stability criteria is considered not met and addition accelerometer data must be obtained.

Once the posture measurement stability criteria is met, in one example, the one or more processors may update the reference standing measurements by taking a median value for each axis from each individual data set. Alternatively, an average value for each axis may be utilized. Still, new updated reference standing measurements are provided that may be utilized for diagnosis determinations, treatment determinations, etc. In one embodiment, in response to the reference standing measurement being updated, the posture detection and identification by the accelerometer, along with determinations made from such accelerometer data is resumed. In this manner, the suspension of accelerometer data use is minimized as a result of the automatic recalibration.

In one example, the suspension lasts a determined suspension period, that in one example can be twenty-four hours, forty-eight hours, or the like. In this manner, during the suspension, x/y/z vector data is collected during determined activities so that a new reference standing measurement can be determined. After the determined suspension period, if enough determined activity accelerometer data is collected, the reference standing measurement is updated, and posture algorithms, and posture-dependent algorithms resume. Alternatively, once the posture measurement stability criteria is met, the posture algorithms, and posture-dependent algorithms resume operating in response to the posture measurement stability criteria being met. In yet another embodiment, a long term average (LTA) of x/y/z vector data is collected during determined activity and is maintained separately, such as in a memory or storage device. The LTA of the x/y/z vector data can then automatically replace the reference standing measurement upon detection of the migration threshold being exceeded. In this manner, the posture prediction algorithm, and other algorithms that depend on the posture algorithm are not impacted, and do not have to be suspended.

Figure 6:
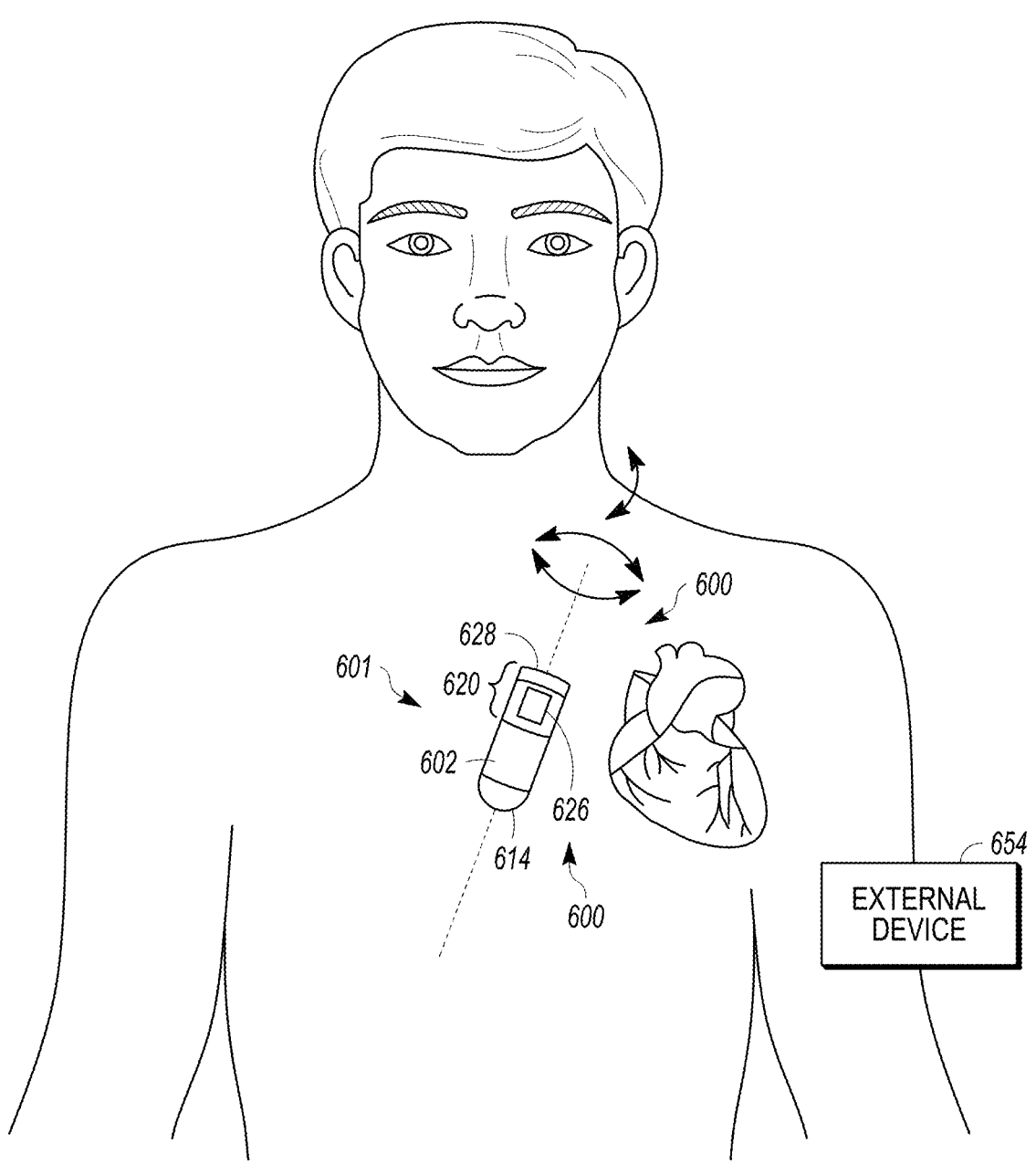
FIG. 6 illustrates an implantable cardiac monitoring device (ICM) intended for subcutaneous implantation at a site near the heart in accordance with embodiments herein.

FIG. 6 illustrates an example monitoring device 600 that is an IMD intended for subcutaneous implantation at a site near the heart that may house a monitoring system 601. In one example the monitoring system 601 is the monitoring system described in FIG. 1. The monitoring device 600 is illustrated as exemplary only, and the monitoring system 601 may be included in other systems. The monitoring device 600 includes two or more spaced-apart sense electrodes 614, 626 positioned with respect to a housing 602. The sense electrodes 614, 626 provide for detection of far field electrogram signals. The header 620 includes an antenna 628 and the electrode 626. The antenna 628 is configured to wirelessly communicate with an external device 654 in accordance with one or more predetermined wireless protocols (e.g., Bluetooth, Bluetooth low energy, Wi-Fi, etc.).

The housing 602 includes various other components such as: sense electronics for receiving signals from the electrodes, a microprocessor for analyzing the far field CA signals, including assessing the presence of R-waves in cardiac beats occurring while the monitoring device is in different locations relative to gravitational force, a loop memory for temporary storage of CA data, a device memory for long-term storage of CA data, sensors for detecting activity of the patient, including an accelerometer for detecting acceleration signatures indicative of heart sound, and a battery for powering components.

The monitoring device 600 may sense far field, subcutaneous CA signals, processes the CA signals to detect arrhythmias and if an arrhythmia is detected, automatically records the CA signals in memory for subsequent transmission to an external device 654.

The monitoring device 600 is implanted in a position and orientation such that, when the patient stands, the monitoring device 600 is located at a reference position and orientation with respect to a global coordinate system that is defined relative to a gravitational direction. For example, the gravitational direction may be along the Z-axis while the X-axis is between the left and right arms.

Figure 7:
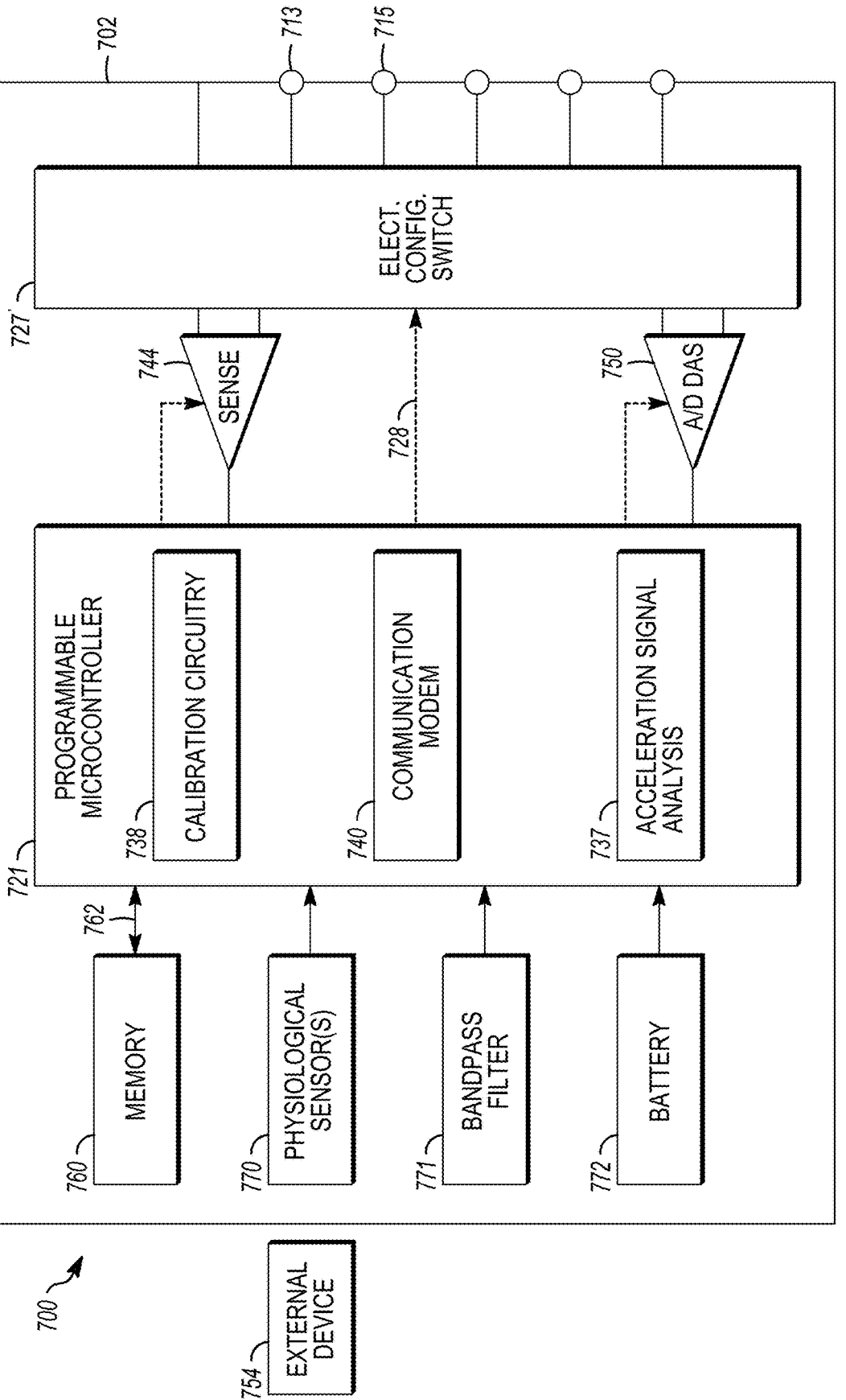
FIG. 7 illustrates a block diagram of the ICM formed in accordance with embodiments herein.

FIG. 7 shows a block diagram of the monitoring device 700 formed in accordance with embodiments herein. The monitoring device 700 has a housing 702 to hold the electronic/computing components. The housing 702 (which is often referred to as the "can", "case", "encasing", or "case electrode") may be programmably selected to act as an electrode for certain sensing modes. Housing 702 further includes a connector (not shown) with at least one terminal 713 and optionally additional terminals 715. The terminals 713, 715 may be coupled to sensing electrodes that are provided upon or immediately adjacent the housing 702. Optionally, more than two terminals 713, 715 may be provided in order to support more than two sensing electrodes, such as for a bipolar sensing scheme that uses the housing 702 as a reference electrode. Additionally or alternatively, the terminals 713, 715 may be connected to one or more leads having one or more electrodes provided thereon, where the electrodes are located in various locations about the heart. The type and location of each electrode may vary.

A switch 727 is optionally provided to allow selection of different electrode configurations under the control of the microcontroller 721. The electrode configuration switch 727 may include multiple switches for connecting the desired electrodes to the appropriate I/O circuits, thereby facilitating electrode programmability. The switch 727 is controlled by a control signal 728 from the microcontroller 721. Optionally, the switch 727 may be omitted and the I/O circuits directly connected via terminals 713, 715.

The monitoring device 600 includes sensing circuit 744 selectively coupled to one or more electrodes that perform sensing operations, through the switch 727 to detect cardiac activity data indicative of cardiac activity. Optionally, the sensing circuit 744 may be removed entirely, and the microcontroller 721 performs the operations described herein based upon the CA signals from the A/D data acquisition system 750 directly coupled to the electrodes. The output of the sensing circuit 744 is connected to the microcontroller 721 which, in turn, determines when to store the cardiac activity data of CA signals (digitized by the A/D data acquisition system 750) in the memory 760.

The monitoring device 600 includes a programmable microcontroller 721 that controls various operations of the monitoring device 600, including cardiac monitoring. Microcontroller 721 includes a microprocessor (or equivalent control circuitry), RAM and/or ROM memory, logic and timing circuitry, state machine circuitry, and I/O circuitry. The microcontroller 721 is configured to implement the acceleration signal analysis 737 operations described herein in connection with collecting and analyzing accelerometer signals.

The microcontroller 721 may also include calibration circuitry 738 that is configured to implement the calibration operations described herein. Among other things, the calibration circuitry 738 obtains baseline accelerometer signals from an accelerometer 770 in connection with patient postures. The postures may include supine, standing, laying on a right side, laying on a left side, angled, or the like. The calibration circuitry 738 may also calculate synthetic baseline accelerometer signals based on orthogonal baseline accelerometer signals that are directly measured by the accelerometer 770 as described herein. Although not shown, the microcontroller 721 may further include a bandpass filter 771 to filter an output of the accelerometer 770 and other dedicated circuitry and/or firmware/software components that assist in monitoring various conditions of the patient's heart and managing pacing therapies.

The monitoring device 700 is further equipped with a communication modem (modulator/demodulator) 740 to enable wireless communication. In one implementation, the communication modem 740 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 740 may be implemented in hardware as part of the microcontroller 721, or as software/firmware instructions programmed into and executed by the microcontroller 721. Alternatively, the modem 740 may reside separately from the microcontroller as a standalone component, or external device 754. The modem 740 facilitates data retrieval from a remote monitoring network. The modem 740 enables timely and accurate data transfer directly from the patient to an electronic device utilized by a physician.

By way of example, the external device 754 may represent a bedside monitor installed in a patient's home and utilized to communicate with the monitoring device 600 while the patient is at home, in bed or asleep. The external device 754 may be a programmer used in the clinic to interrogate the monitoring device 600, retrieve data and program detection criteria and other features. The external device 754 may be a PDE (e.g., smartphone, tablet device, laptop computer, smartwatch, and the like) that can be coupled over a network (e.g., the Internet) to a remote monitoring service, medical network and the like. The external device 754 facilitates access by physicians to patient data as well as permitting the physician to review real-time accelerometer data sets as collected by the monitoring device 600.

The microcontroller 721 is coupled to a memory 760 by a suitable data/address bus 762. The memory 760 stores the accelerometer signals, accelerometer data sets, reference posture related data sets, cardiac activity signals, as well as the markers and other data content associated with detection and determination of the condition of the heart of the patient.

The monitoring device 600 can further include one or more accelerometer circuits 770. For example, the accelerometer circuits 770 may be part of a monitoring system 701, or may represent one or more accelerometers, such as a three-dimensional (3D) accelerometer. The accelerometer circuits 770 may utilize a piezoelectric, a piezoresistive, and/or capacitive components are commonly used to convert the mechanical motion of the 3D accelerometer into an electrical signal received by the microcontroller 721. By way of example, the 3-D accelerometer may three outputs/channels that generate three corresponding electrical signals indicative of motion in three corresponding directions, namely X, Y and Z directions. The electrical signals associated with each of the three directional components may be divided into different frequency components to obtain different types of information therefrom.

The accelerometer circuits 770 collect device location information with respect to gravitational force while the monitoring device 600 collects cardiac activity signals in connection with multiple cardiac beats. In one example, the accelerometer circuits 770 include the accelerometer as described in relation to FIG. 1. The microcontroller 721 may utilize the signals from the accelerometer circuits 770. While shown as being included within the housing 602, the accelerometer circuit 770 may be external to the housing 602, yet still, be implanted within or carried by the patient.

The accelerometer circuits 770 can obtain accelerometer data and communicate with sensors, other electronic devices, etc. to identify that the patient is engaged in a determined activity. The determined activity is indicative of the patient having a standing posture. The accelerometer circuits 770 can then compare a reference standing measurement from an initial position to the accelerometer data collected during the activity period. From this comparison, a determination can be made that migration of the monitoring device has occurred. If a threshold migration is detected, the accelerometer circuits 770 suspend obtaining accelerometer readings and accelerometer based determinations until the accelerometer is recalibrated to provide an updated reference standing measurement. In one example, the accelerometer circuits 770 may obtain activity data from previous activity periods of determined activities to automatically recalibrate the accelerometer. Once recalibrated, the accelerometer can resume the operation of accelerometer.

A battery 772 provide operating power to all of the components in the monitoring device 600. The battery 772 is capable of operating at low current drains for long periods of time. The battery 772 also desirably has a predictable discharge characteristic so that elective replacement time can be detected.

Figure 8:
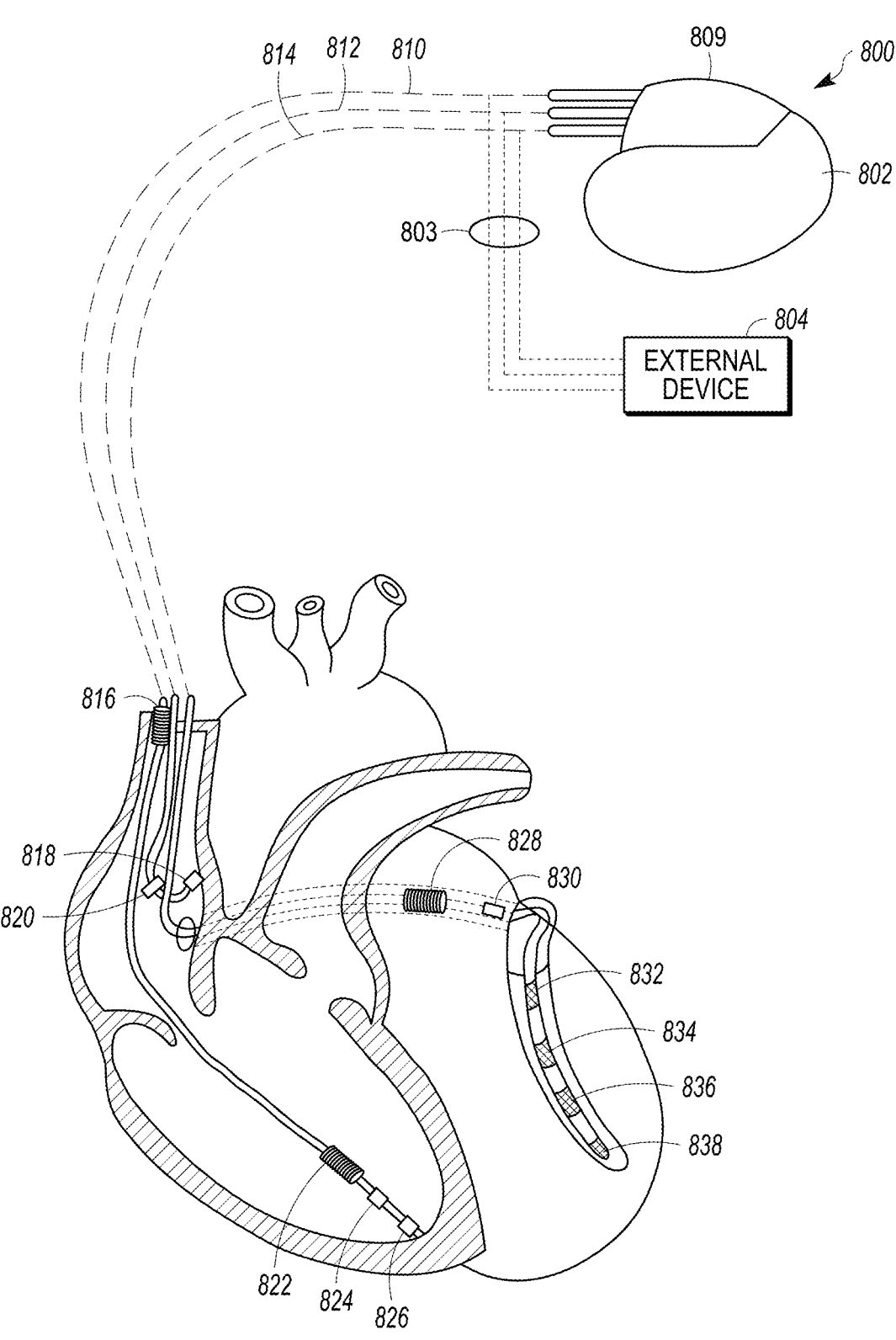
FIG. 8 illustrates an implantable medical device (IMD) intended for subcutaneous implantation at a site near the heart in accordance with embodiments herein.

FIG. 8 illustrates an alternative monitoring device 800 that may apply treatment, such as a shock when a candidate pathologic episode such as VF or VT is verified using the method of FIG. 3. The monitoring device 800 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The monitoring device 800 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the monitoring device 800 are discussed and illustrated in the drawings herewith.

The monitoring device 800 includes a housing 802 that is joined to a header assembly 809 that holds receptacle connectors connected to a right ventricular lead 810, a right atrial lead 812, and a coronary sinus lead 814, respectively. The leads 812, 814 and 810 measure cardiac signals of the heart. The right atrial lead 812 includes an atrial tip electrode 818 and an atrial ring electrode 820. The coronary sinus lead 814 includes a left atrial ring electrode 828, a left atrial coil electrode 830 and one or more left ventricular electrodes 832-838 (e.g., also referred to as P1, M1, M2 and D1) to form a multi-pole LV electrode combination. The right ventricular lead 810 includes an RV tip electrode 826, an RV ring electrode 824, an RV coil electrode 822, and an SVC coil electrode 816. The leads 812, 814 and 810 detect IEGM signals that are processed and analyzed as described herein. The leads 812, 814 and 810 also delivery therapies as described herein.

During implantation, an external device 804 is connected to one or more of the leads 812, 814 and 810 through temporary inputs 803. The inputs 803 of the external device 804 receive IEGM signals from the leads 812, 814 and 810 during implantation and display the IEGM signals to the physician on a display. Hence, the external device 804 receives the IEGM cardiac signals through telemetry circuit inputs. The physician or another user controls operation of the external device 804 through a user interface.

Figure 9:
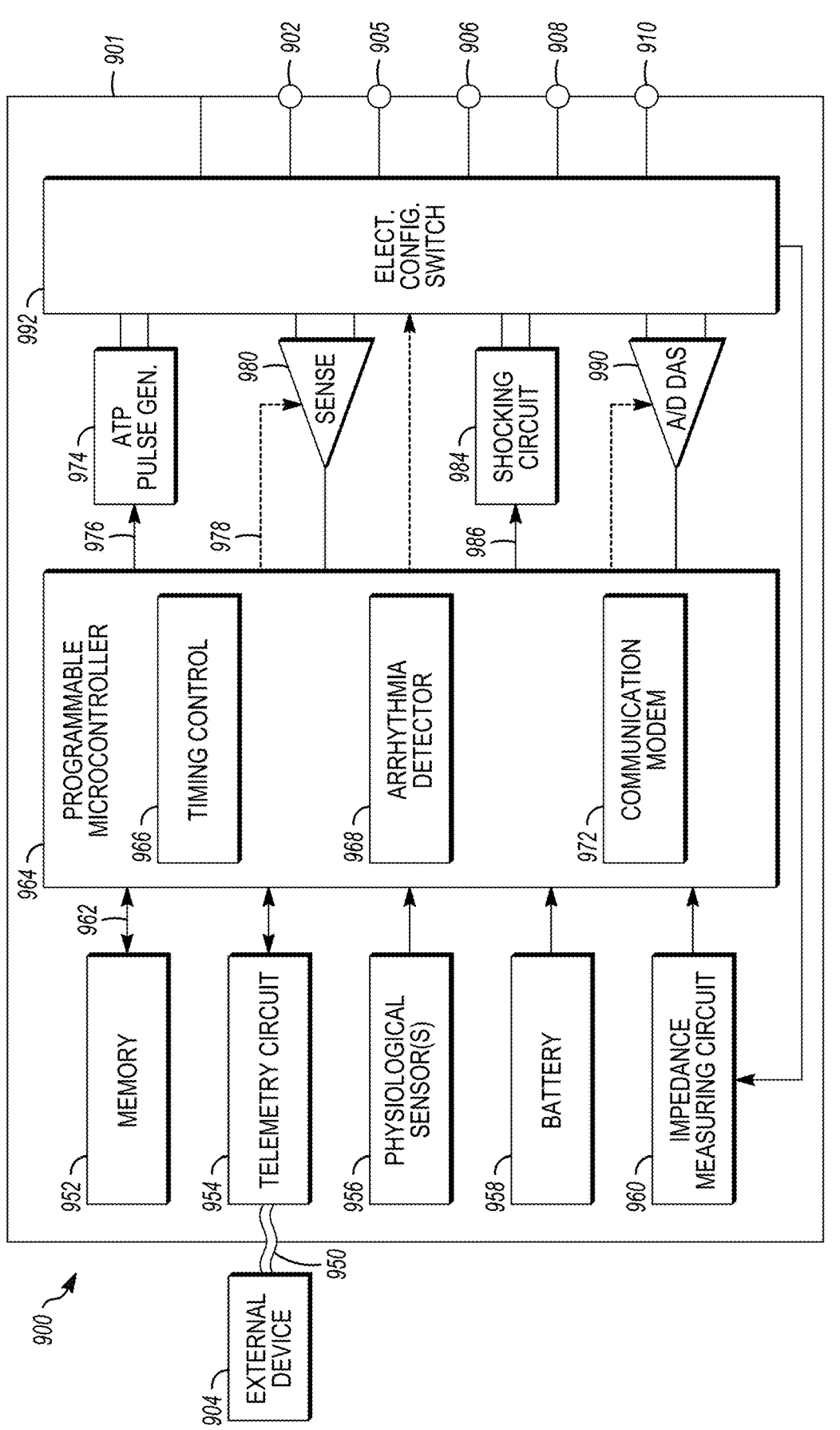
FIG. 9 illustrates a block diagram of the IMD formed in accordance with embodiments herein.

FIG. 9 illustrates an example block diagram of a monitoring device 900 that is implanted into the patient as part of the implantable cardiac system. In one example, the monitoring device 900 is an IMD. The monitoring device 900 may be implemented as a full-function biventricular pacemaker, equipped with both atrial and ventricular sensing and pacing circuitry for four chamber sensing and stimulation therapy (including both pacing and shock treatment). Optionally, the monitoring device 900 may provide full-function cardiac resynchronization therapy. Alternatively, the monitoring device 900 may be implemented with a reduced set of functions and components. For instance, the monitoring device may be implemented without ventricular sensing and pacing.

The monitoring device 900 has a housing 901 to hold the electronic/computing components. The housing 901 (which is often referred to as the "can", "case", "encasing", or "case electrode") may be programmably selected to act as the return electrode for certain stimulus modes. Housing 901 further includes a connector (not shown) with a plurality of terminals 902, 905, 906, 908, and 910. The type and location of each electrode may vary. For example, the electrodes may include various combinations of ring, tip, coil and shocking electrodes and the like.

The monitoring device 900 includes a programmable microcontroller 964 that controls various operations of the monitoring device 900. Microcontroller 964 includes a microprocessor (or equivalent control circuitry), RAM and/ or ROM memory, logic and timing circuitry, state machine circuitry, and I/O circuitry. The monitoring device 900 further includes a first chamber pulse generator 974 that generates stimulation pulses for delivery by one or more electrodes coupled thereto. The pulse generator 974 is controlled by the microcontroller 964 via control signal 976. The pulse generator 974 is coupled to the select electrode(s) via an electrode configuration switch 992, which includes multiple switches for connecting the desired electrodes to the appropriate I/O circuits, thereby facilitating electrode programmability. The switch 992 is controlled by a control signal 986 from the microcontroller 964.

Microcontroller 964 is illustrated to include timing control circuitry 966 to control the timing of the stimulation pulses (e.g., pacing rate, atrio-ventricular (AV) delay, atrial interconduction (A-A) delay, or ventricular interconduction (V-V) delay, etc.). Microcontroller 964 also has an arrhythmia detector 968 for detecting arrhythmia conditions. Although not shown, the microcontroller 964 may further include other dedicated circuitry and/or firmware/software components that assist in monitoring various conditions of the patient's heart and managing pacing therapies.

The monitoring device 900 is further equipped with a communication modem (modulator/demodulator) 972 to enable wireless communication with other devices, implanted devices, and/or external devices. The monitoring device 900 includes sensing circuitry 980 selectively coupled to one or more electrodes that perform sensing operations, through the switch 992, to detect the presence of cardiac activity.

The output of the sensing circuitry 980 is connected to the microcontroller 964 which, in turn, triggers or inhibits the pulse generator 974 in response to the absence or presence of cardiac activity. The sensing circuitry 980 receives a control signal 978 from the microcontroller 964 for purposes of controlling the gain, threshold, polarization charge removal circuitry (not shown), and the timing of any blocking circuitry (not shown) coupled to the inputs of the sensing circuitry.

In the example of FIG. 9, a single sensing circuit 980 is illustrated. Optionally, the monitoring device 900 may include multiple sensing circuit, similar to sensing circuit 980, where each sensing circuit is coupled to one or more electrodes and controlled by the microcontroller 964 to sense electrical activity detected at the corresponding one or more electrodes. The sensing circuit 980 may operate in a unipolar sensing configuration or in a bipolar sensing configuration.

The monitoring device 900 further includes an analog-to-digital (A/D) data acquisition system (DAS) 990 coupled to one or more electrodes via the switch 992 to sample cardiac signals across any pair of desired electrodes. The microcontroller 964 is also coupled to a memory 952 by a suitable data/address bus 962. The programmable operating parameters used by the microcontroller 964 are stored in memory 952 and used to customize the operation of the monitoring device 900 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The telemetry circuit 954 allows intracardiac electrograms and status information relating to the operation of the monitoring device 900 (as contained in the microcontroller 964 or memory 952) to be sent to the external device 904 through the established communication link 950.

The monitoring device 900 can further include one or more physiologic sensors 956. Such sensors are commonly referred to as "rate-responsive" sensors because they are typically used to adjust pacing stimulation rates according to the exercise state of the patient. However, the physiological sensor 956 may further be used to detect changes in cardiac output, changes in the physiological condition of the heart, or diurnal changes in activity (e.g., detecting sleep and wake states).

A battery 958 provides operating power to all of the components in the monitoring device 900. The monitoring device 900 further includes an impedance measuring circuit 960, which can be used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. The impedance measuring circuit 960 is coupled to the switch 992 so that any desired electrode may be used. The monitoring device 900 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 964 further controls a shocking circuit 984 by way of a control signal 986.

Figure 10:
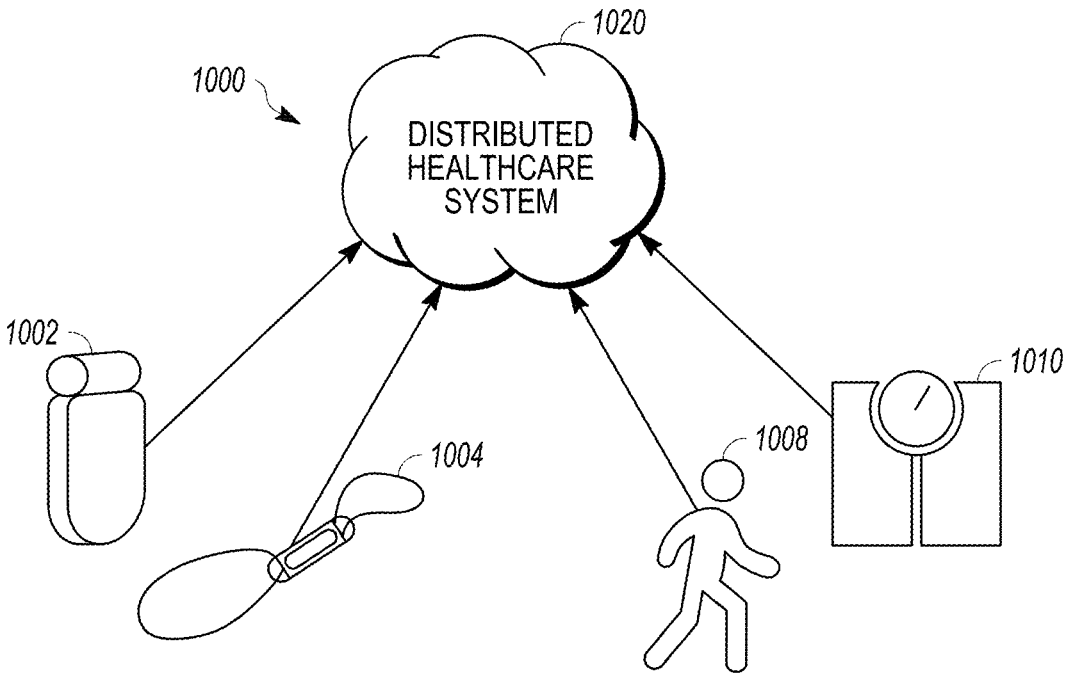
FIG. 10 illustrates a schematic diagram of a healthcare system in accordance with embodiments herein.

FIG. 10 illustrates a digital healthcare system 1000 implemented in accordance with embodiments herein. The system 1000 integrates accelerometer signals and the other information derived from accelerometer signals with other health data in connection with monitor a patient condition, progression of a health condition, trends in a patient's health condition, treatment, changes in therapy/medication and the like. The healthcare system 1000 may include wearable PDE that communicate with an IMD or accelerometer and a remote database. As a result, the healthcare system 1000 may monitor health parameters of patient, including MD accelerometer data and TR parameters, and provide a diagnosis for the patient based on the monitored health parameters.

The system may be implemented with various architectures, that are collectively referred to as a healthcare system 1020. By way of example, the healthcare system 1020 may be implemented as described herein. The healthcare system 1020 is configured to receive data from a variety of external and implantable sources including, but not limited to, active IMDs 1002 capable of delivering therapy to a patient, passive IMDs or sensors 1004, wearable sensors 1008, and point-of-care (POC) devices 1010 (e.g., at home or at a medical facility). Any of the IMD 1002, sensor 1004, and/or sensor 1008 may implement an accelerometer circuitry and perform the analysis of accelerometer signals as described herein. The data from one or more of the external and/or implantable sources is collected and communicated to one or more secure databases within the healthcare system 1020. Optionally, the patient and/or other users may utilize a PDE device, such as a smart phone, tablet device, etc., to enter data. For example, a patient may use a smart phone to provide feedback concerning activities performed by the patient, a patient diet, nutritional supplements and/or medications taken by the patient, how a patient is feeling (e.g., tired, dizzy, weak, good), etc.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for determining a change in position of an implanted medical device (IMD) within an implant pocket, the system comprising:

an accelerometer configured to be implanted in a patient, the accelerometer configured to obtain accelerometer data along at least one axis;

memory configured to store program instructions;

one or more processors that, when executing the program instructions, are configured to:

determine when the patient is engaging in a determined activity associated with a standing posture;

responsive to the determination, obtain the accelerometer data during an activity period;

identify postures, indicated by the accelerometer data, over the activity period, the postures including a non-standing posture;

determine a duration of one or more posture periods corresponding to the non-standing posture; and identify a migration of the IMD within the implant pocket based on the duration of the non-standing posture exceeding a duration threshold.

2. The system of claim 1, wherein the one or more processors are further configured to:

determine an extent of the migration of the IMD within the implant pocket based on the accelerometer data; and suspend obtaining the accelerometer data when the extend of the migration exceeds a migration threshold.

3. The system of claim 2, wherein the migration threshold is a fifteen degree (15°) rotation.

4. The system of claim 2, wherein the one or more processors are further configured to:

recalibrate a reference standing measurement related to a standing posture after suspending the obtaining of the accelerometer data; and resume obtaining the accelerometer data in response to recalibration of the reference standing measurement.

5. The system of claim 1, wherein to recalibrate a reference standing measurement the one or more processors are configured to:

obtain plural readings along an x-axis, y-axis, and z-axis with the accelerometer during the activity period;

determine a standard deviation based on the plural readings; and update the reference standing measurement based on the standard deviation.

6. The system of claim 1, wherein the one or more processors are further configured to: communicate an alert in response to identifying the migration of the IMD within the implant pocket.

7. The system of claim 1, wherein the one or more processors are further configured to: automatically recalibrate a reference standing measurement related to a standing posture in response to identifying the migration of the IMD within the implant pocket.

8. The system of claim 1, wherein to determine the patient is engaging in the determined activity, the one or more processors are further configured to: determine whether the patient is moving above a speed threshold, or determine physiological characteristics of the patient.

9. A computer implemented method for determining a change in position of an implanted medical device (IMD) within a patient, the method comprising:

determining when the patient is engaging in a determined activity associated with a standing posture;

responsive to the determining, obtaining accelerometer data during an activity period;

identifying postures, indicated by the accelerometer data, over the activity period, the postures including a non-standing posture;

determining a duration of one or more posture periods corresponding to the non-standing posture; and identifying a migration of the IMD within the implant pocket based on the duration of the non-standing posture exceeding a duration threshold.

10. The method of claim 9, further comprising:

determining an extent of the migration of the IMD within the implant pocket based on the accelerometer data; and suspending obtaining the accelerometer data when the extent of the migration exceeds a migration threshold.

11. The method of claim 10, further comprising:

recalibrating a reference standing measurement related to a standing posture after suspending the obtaining of the accelerometer data; and resuming obtaining the accelerometer data in response to recalibration of the reference standing measurement.

12. The method of claim 9, further comprising, recalibrating the reference standing measurement by:

obtaining plural readings along an x-axis, y-axis, and z-axis with an accelerometer during the activity period;

determining a standard deviation based on the plural readings; and updating the reference standing measurement based on the standard deviation.

13. The method of claim 9, further comprising communicating an alert in response to identifying the migration of the IMD within the implant pocket.

14. The method of claim 9, further comprising automatically recalibrating a reference standing measurement related to a standing posture in response to identifying the migration of the IMD within the implant pocket.

15. The method of claim 14, wherein automatically recalibrating the reference standing measurement includes obtaining a long term average of x-axis, y-axis, and z-axis vector data from one or more previous activity periods.

16. The method of claim 9, wherein determining the patient is engaging in the determined activity comprises determining whether the patient is moving above a speed threshold.

17. The method of claim 9, wherein determining the patient is engaging in the determined activity comprises determining physiological characteristics of the patient.

18. The system of claim 1, wherein, during the activity period and while the patient maintains the standing posture, the accelerometer data indicates the non-standing posture due to the migration of the IMD within the implant pocket.

19. The system of claim 1, wherein the one or more processors are further configured to calculate, over at least a portion of the determined activity, at least one of an extent of right (ETR) or extent of supine (ETS) parameter based on the accelerometer data, the migration identified in part based on at least one of the ETR or ETS parameter.

20. The system of claim 1, wherein the at least one of the ETR or ETS provides a degree tilt, flip, rotation or angle of an orientation of the IMD with respect to a standing posture, the migration identified in part based on an expected ETR or ETS value when the patient is in the engaged in the determined activity.

21. The method of claim 9, wherein, during the activity period and while the patient maintains the standing posture, the accelerometer data indicates the non-standing posture due to the migration of the IMD within the implant pocket.

* * * * *